United States Patent
Bender et al.

(10) Patent No.: US 6,417,181 B1
(45) Date of Patent: Jul. 9, 2002

(54) NAPHTHYL-SUBSTITUTED AND ANILIDE-SUBSTITUTED SULFONAMIDES

(75) Inventors: Wolfgang Bender; Jürgen Reefschläger; Peter Eckenberg; Siegfried Goldmann, all of Wuppertal; Michael Härter, Leverkusen; Sabine Hallenberger, Wuppertal, all of (DE); Jörg Trappe, Monza (IT); Olaf Weber, Wülfrath (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/600,750

(22) PCT Filed: Jan. 9, 1999

(86) PCT No.: PCT/EP99/00099
§ 371 (c)(1),
(2), (4) Date: Sep. 1, 2000

(87) PCT Pub. No.: WO99/37609
PCT Pub. Date: Jul. 29, 1999

(30) Foreign Application Priority Data

Jan. 23, 1998 (DE) ......................................... 198 02 439

(51) Int. Cl.$^7$ .......................... A61K 31/17; A61K 31/44
(52) U.S. Cl. ....................... 514/183; 514/293; 514/300; 514/311; 544/159
(58) Field of Search ........................ 544/159; 514/183, 514/293, 300, 311

(56) References Cited

U.S. PATENT DOCUMENTS

| | | | |
|---|---|---|---|
| 2,423,572 A | * 7/1947 | Woodward | 260/338 |
| 2,949,479 A | * 8/1960 | Ueda et al. | 260/401 |
| 3,482,971 A | 12/1969 | Bloom et al. | 96/3 |
| 3,622,603 A | 11/1971 | Bloom et al. | 260/397.7 |
| 3,925,347 A | 12/1975 | Huyffer | 260/147 |
| 4,035,401 A | 7/1977 | Huyffer | 260/404.5 |
| 4,289,847 A | 9/1981 | Ishikawa et al. | 430/389 |
| 4,855,223 A | 8/1989 | Vanmaele et al. | 430/562 |
| 5,646,121 A | 7/1997 | Häbach et al. | 514/18 |

FOREIGN PATENT DOCUMENTS

| | | | |
|---|---|---|---|
| DE | 4331134 | 3/1995 | C07K/5/06 |
| EP | 0684515 | 11/1995 | G03C/7/305 |
| WO | 9009787 | 9/1990 | A61K/31/17 |
| WO | WO-9009787 | * 9/1990 | |

OTHER PUBLICATIONS

Sorbera et al. "Bay–38–4766: anti–cytomegalovirus drug", HCAPLUS 133:37556, Drugs Future (1999), 24(12), 1297–1300.*

Pant, U. C., and Joshi, B. C., "Studies on 2–Hydroxy–3–Naphthoic Acid–1–Sulphonamides and 4–Hydroxy–3–Naphthoic Acid–1–Sulphonamides", J. Inst. Chemists (India) 48: 280–285 (1976).

*Printing; Coating; Photographic Chemistry*, p. 9, J5–G, Week 8446, FUJF, 84–284688/46, J59174–836–A, "Silver halide color photographic sensive material contains coupler having naphthalene nucleus having at least one hydroxyl and sulphonyl or sulphinyl", Fuji Photo Film KK, 25.03.83, JP–050001.

Derwent Abstract, Accession No. 0D1994–186388 [23], "Phospholipase A2 inhibitors comprise new diaminobenzene cpds.—for the treatment and pancreatitis", (ISHH) Ishihara Sangyo Kaisha Ltd., JP–06122669–A, 06/05/94.

S.–W. Jin, "A New Sensitive Edman–type Reagent: 4–(N–1–dimethylamino–naphthalene–5–sulphonylamino)–phenyl isothiocyanate", FEBS Letters, 198(1): 150–154 (Mar. 1986).

* cited by examiner

*Primary Examiner*—Ralph Gitomer
*Assistant Examiner*—Devesh Khare
(74) *Attorney, Agent, or Firm*—Jerrie L. Chiu

(57) ABSTRACT

The present invention relates to new naphthyl- and anilide-substituted sulphonamides of the general formula (I)

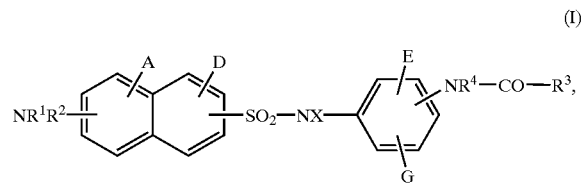

(I)

in which the substituents A, D, E, G, $R^1$, $R^2$, $R^3$, $R^4$ and X have the meanings indicated, and to processes for their preparation and their use as antiviral agents, in particular against cytomegaloviruses.

16 Claims, No Drawings

NAPHTHYL-SUBSTITUTED AND ANILIDE-SUBSTITUTED SULFONAMIDES

The present invention relates to new naphthyl- and anilide-substituted sulphonamides, processes for their preparation and their use as antiviral agents, in particular against cytomealoviruses.

α,β-Naphthyl-linked phenylsulphonamides are mainly disclosed in phototechnical publications [cf. for this purpose JP-06 122 669-A2, EP-684 515-A1; JP-59 174 836-A2, DE-2 902 074, U.S. Pat. No. 3,925,347, U.S. Pat. No. 4,035,401, U.S. Pat. No. 3,622,603, U.S. Pat. No. 3,482,971, EP-284 130].

WO 90/09 787 discloses sulphonamides as radio- or chemosensitizing agents and their use in the treatment of tumours.

The compound N-[4-[[[5-(dimethylamino)-1-naphthalenyl]sulphonyl]amino]phenyl]-acetamide is additionally known (J. Inst. Chem. (India) (1976), 4S. Pt 6, 280-5).

The present invention relates to new naphthyl- and anilide-substituted sulphonamides of the general formula (I)

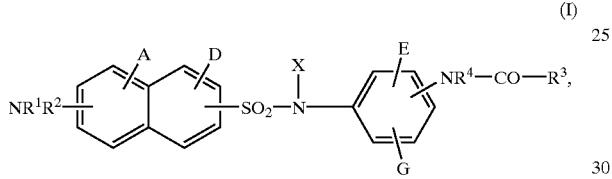

(I)

in which
  $R^1$ and $R^2$ are identical or different and represent hydrogen, formyl, phenyl or benzyl optionally substituted by one to three halogen atoms, or straight-chain or branched alkyl or acyl each having up to 6 carbon atoms, where alkyl or acyl can optionally be substituted by one to three substituents selected from halogen and hydroxyl,
  A, D, E and G are identical or different and represent hydrogen, halogen, nitro, cyano, hydroxyl, carboxyl, trifluoromethyl, trifluoromethoxy or straight-chain or branched alkyl, alkoxy or alkoxycarbonyl each having up to 5 carbon atoms,
  $R^3$ represents straight-chain or branched alkenyl having up to 6 carbon atoms, or represents straight-chain or branched alkyl having up to 8 carbon atoms, which optionally carries an amino group which can optionally be substituted by alkyl having up to 4 carbon atoms or by an amino protective group, or the alkyl is optionally identically or differently substituted one to 3 times by hydroxyl, cyano, halogen, azido, nitro, trifluoromethyl, carboxyl or phenyl which, for its part, can be identically or differently substituted up to 2 times by nitro, halogen, hydroxyl or by straight-chain or branched alkyl or alkoxy having up to 4 carbon atoms, or
  $R^3$ represents radicals of the formula

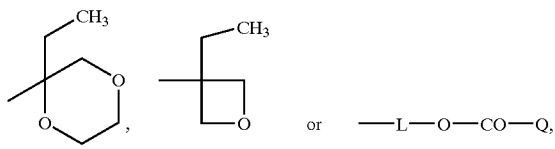

or —L—O—CO—Q, in which
  L represents a straight-chain or branched alkanediyl group having up to 6 carbon atoms,
  Q represents alkyl having up to 6 carbon atoms, which is optionally substituted by carboxyl, or represents radicals of the formula

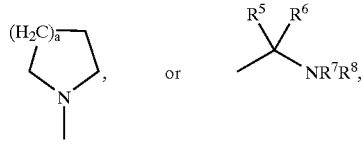

in which
  a denotes the number 1 or 2,
  $R^5$ denotes hydrogen,
  $R^6$ denotes cycloalkyl having 3 to 8 carbon atoms or aryl having 6 to 10 carbon atoms or hydrogen, or denotes straight-chain or branched alkyl having up to 8 carbon atoms,
  where the alkyl is optionally substituted by cyano, methylthio, hydroxyl, mercapto, guanidyl or by a group of the formula —$NR^9R^{10}$ or $R^{11}$—OC—,
    in which
    $R^9$ and $R^{10}$ independently of one another denote hydrogen, straight-chain or branched alkyl having up to 8 carbon atoms or phenyl,
    and
    $R^{11}$ denotes hydroxyl, benzyloxy, alkoxy having up to 6 carbon atoms or the abovementioned group —$NR^9R^{10}$,
  or the alkyl is optionally substituted by cycloalkyl having 3 to 8 carbon atoms or by aryl having 6 to 10 carbon atoms, which, for its part, is substituted by hydroxyl, halogen, nitro, alkoxy having up to 8 carbon atoms or by the group —$NR^9R^{10}$,
    in which
    $R^9$ and $R^{10}$ have the meaning indicated above,
  or the alkyl is optionally substituted by a 5- to 6-membered nitrogen-containing heterocycle or by indolyl, in which the corresponding —NH functions are optionally substituted by alkyl having up to 6 carbon atoms or protected by an amino protective group,
  $R^7$ and $R^8$ are identical or different and denote hydrogen or an amino protective group,
  $R^4$ represents hydrogen or a radical of the formula

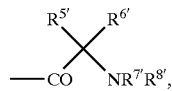

in which
  $R^{5'}$, $R^{6'}$, $R^{7'}$ and $R^{8'}$ have the meaning of $R^6$, $R^7$ and $R^8$ indicated above and are identical to or different from this,
  X has the meaning of $R^4$ indicated above and can be identical to or different from this meaning,
and their stereoisomers, stereoisomeric mixtures and salts, with the exception of N-[4-[[[5-(dimethylamino)-1-naphthalenyl]sulphonyl]amino]phenyl]acetamide.

In a preferred embodiment, the invention relates to sulphonamides of the above general formula (I), in which
  $R^1$ and $R^2$ are identical or different and represent hydrogen, phenyl or straight-chain or branched alkyl or acyl each having up to 6 carbon atoms A, D, E and G are identical or different and represent hydrogen, halogen, nitro, cyano, hydroxyl, carboxyl, trifluoromethyl, trifluoromethoxy or straight-chain or branched alkyl, alkoxy or alkoxycarbonyl each having up to 5 carbon atoms, $R^3$ represents straight-chain or branched alkenyl having up to 6 carbon atoms, or represents straight-chain or branched alkyl having up to 8 carbon atoms. which optionally carries an amino group which can be substituted by alkyl having up to 4 carbon atoms or by an amino protective group, or the alkyl is optionally identically or differently substituted one to 3 times by hydroxyl, cyano, halogen, azido, nitro, trifluoromethyl, carboxyl or phenyl which, for its part, can be identically or differently substituted up to 2 times by nitro, halogen, hydroxyl or by straight-chain or branched alkyl or alkoxy having up to 4 carbon atoms, or $R^3$ represents radicals of the formula

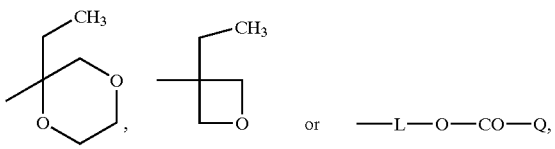

in which

L represents a straight-chain or branched alkanediyl group having up to 6 carbon atoms, Q represents alkyl having up to 6 carbon atoms, which is optionally substituted by carboxyl, or represents radicals of the formula

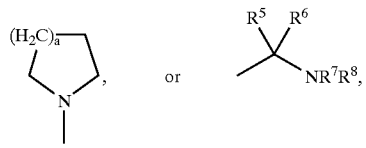

in which a denotes the number 1 or 2, $R^5$ denotes hydrogen, $R^6$ denotes cycloalkyl having 3 to 8 carbon atoms or aryl having 6 to 10 carbon atoms or hydrogen, or denotes straight-chain or branched alkyl having up to 8 carbon atoms, where the alkyl is optionally substituted by cyano, methylthio, hydroxyl, mercapto, guanidyl or by a croup of the formula —$NR^9R^{10}$ or $R^{11}$—OC—, in which $R^9$ and $R^{10}$ independently of one another denote hydrogen, straight-chain or branched alkyl having up to 8 carbon atoms or phenyl, and $R^{11}$ denotes hydroxyl, benzyloxy, alkoxy having up to 6 carbon atoms or the abovementioned group —$NR^9R^{10}$, or the alkyl is optionally substituted by cycloalkyl having 3 to 8 carbon atoms or by aryl having 6 to 10 carbon atoms which, for its part, is substituted by hydroxyl, halogen, nitro, alkoxy having up to 8 carbon atoms or by the group —$NR^9R^{10}$, in which $R^1$ and $R^{10}$ having the meaning indicated above, or the alkyl is optionally substituted by a 5- to 6-membered nitrogen-containing heterocycle or by indolyl, in which the corresponding —NH functions are optionally substituted by alkyl having up to 6 carbon atoms or protected by an amino protective group, $R^7$ and $R^8$ are identical or different and denote hydrogen or an amino protective group, $R^4$ represents hydrogen or a radical of the formula

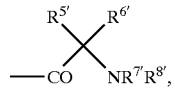

in which $R^{5'}$, $R^{6'}$, $R^{7'}$ and $R^{8'}$ have the meaning of $R^5$, $R^6$, $R^7$ and $R^8$ indicated above and are identical to or different from these, and X represents hydrogen, and their stereoisomers, stereoisomeric mixtures and salts, with the exception of N-[4-[[[5-(dimethylamino)-1-naphthalenyl]sulphonyl]amino]-phenyl]acetamide.

Further preferred compounds are sulphonamides of the above general formula (I), in which $R^3$ represents straight-chain or branched alkenyl having up to 6 carbon atoms, or represents straight-chain or branched alkyl having up to 8 carbon atoms, in which the alkyl carries an amino group which can be substituted by alkyl having up to 4 carbon atoms or by an amino protective group, or the alkyl is identically or differently substituted one to 3 times by hydroxyl, cyano, halogen, azido, nitro, trifluoromethyl, carboxyl or phenyl which. for its part, can be identically or differently substituted up to 2 times by nitro, halogen or hydroxyl or by straight-chain or branched alkyl or alkoxy having up to 4 carbon atoms, or $R^3$ represents radicals of the formula

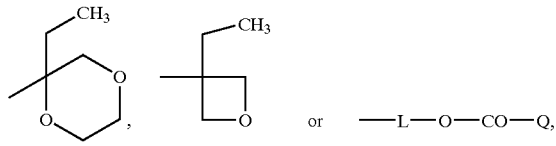

in which L and Q are as defined above, and X preferably represents hydrogen.

Further preferred compounds of the invention are sulphonamides of the above general formula (I), in which $R^1$ and $R^2$ are identical or different and represent hydrogen, phenyl or straight-chain or branched alkyl or acyl each having up to 5 carbon atoms, A, D, E and G are identical or different and represent hydrogen, fluorine, chlorine, bromine, nitro, cyano, hydroxyl or straight-chain or branched alkyl, alkoxy or alkoxycarbonyl each having up to 3 carbon atoms, $R^3$ represents straight-chain or branched alkenyl having up to 5 carbon atoms, or represents straight-chain or branched alkyl having up to 7 carbon atoms, which optionally carries an amino group which can be substituted by alkyl having up to 3 carbon atoms, tert-butyloxycarbonyl or benzyloxycarbonyl, or the alkyl is optionally identically or differently substituted one to 3 times by hydroxyl, cyano, fluorine, chlorine, azido, nitro, trifluoromethyl or phenyl which, for its part, can be identically or differently substituted up to 2 times by nitro, fluorine, chlorine or hydroxyl or by straight-chain or branched alkyl or alkoxy having up to 3 carbon atoms, or $R^3$ represents radicals of the formula

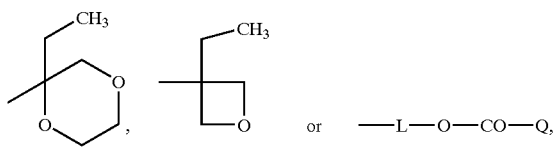 or —L—O—CO—Q, in which
L represents a straight-chain or branched alkanediyl group having up to 4 carbon atoms,
Q represents alkyl having up to 4 carbon atoms, which is optionally substituted by carboxyl, or represents radicals of the formula

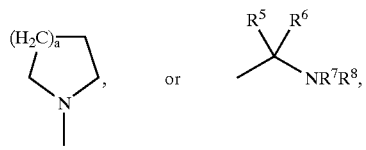

in which
a denotes the number 1 or 2,
$R^5$ denotes hydrogen,
$R^6$ denotes cyclopentyl, cyclohexyl, phenyl or hydrogen, or denotes straight-chain or branched alkyl having up to 6 carbon 10 atoms.
where the alkyl can optionally be substituted by cyano, methylthio, hydroxyl, mercapto, guanidyl, amino, carboxyl or $H_2N$—CO—,
or the alkyl is substituted by cyclohexyl, naphthyl or phenyl which, for its part, can be substituted by fluorine, hydroxyl, nitro or alkoxy having up to 4 carbon atoms,
or the alkyl is substituted by indolyl, imidazolyl, pyridyl, triazolyl or pyrazolyl, where the corresponding —NH functions are optionally substituted by alkyl having up to 4 carbon atoms or protected by tert-butyloxycarbonyl or benzyloxycarbonyl,
$R^7$ and $R^8$ are identical or different and denote hydrogen, tert-butyloxycarbonyl or benzyloxycarbonyl,
$R^4$ represents hydrogen or a radical of the formula

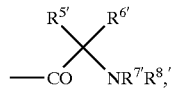

in which
$R^{5'}$, $R^{6'}$, $R^{7'}$ and $R^{8'}$ have the meaning of $R^5$, $R^6$, $R^7$ and $R^8$ indicated above and are identical to or different from this, and
X preferably represents hydrogen,
and their stereoisomers, stereoisomeric mixtures and salts with the exception of N-[4-[[[5-(dimethylamino)-1-naphthalenyl]sulphonyl]amino]phenyl]acetamide.

Further preferred compounds of the invention are sulphonamides of the above general formula (I), in which
$R^3$ represents straight-chain or branched alkenyl having up to 5 carbon atoms, or represents straight-chain or branched alkyl having up to 7 carbon atoms, in which the alkyl carries an amino group which can be substituted by alkyl having up to 3 carbon atoms, tert-butyloxycarbonyl or benzyloxycarbonyl, or the alkyl is identically or differently substituted one to 3 times by hydroxyl, cyano, fluorine, chlorine, azido, nitro, trifluoromethyl or phenyl which, for its part, can be identically or differently substituted up to 2 times by nitro, fluorine. chlorine or hydroxyl or by straight-chain or branched alkyl or alkoxy having up to 3 carbon atoms, or
$R^3$ represents radicals of the formula

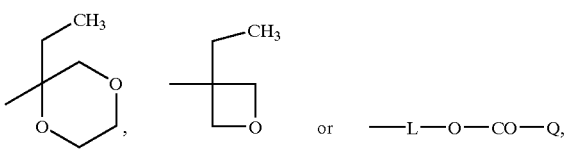

and in which L and Q are as defined above
X preferably represents hydrogen,
Further preferred compounds of the invention are sulphonamides of the above general formula (I), in which
$R^1$ and $R^2$ are identical or different and represent hydrogen, phenyl or straight-chain or branched alkyl or acyl each having up to 4 carbon atoms,
A, D, E and G are identical or different and represent hydrogen, fluorine, chlorine, bromine, hydroxyl, methyl or methoxy,
$R^3$ represents straight-chain or branched alkenyl having up to 4 carbon atoms, or represents straight-chain or branched alkyl having up to 5 carbon atoms, which optionally carries an amino group which can be substituted by tert-butyloxycarbonyl or benzyloxycarbonyl, or which is optionally identically or differently substituted one to 3 times by hydroxyl, cyano, fluorine, chlorine, nitro, azido, trifluoromethyl or phenyl which, for its part, can be identically or differently substituted up to 2 times by nitro, fluorine, chlorine, hydroxyl, methyl, ethyl, methoxy or ethoxy, or
$R^3$ represents radicals of the formula

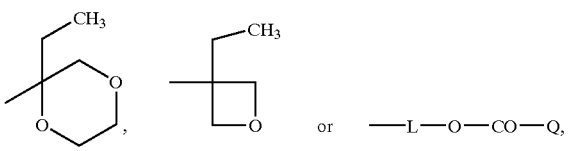

in which
L represents a straight-chain or branched alkanediyl group having up to 4 carbon atoms,
Q represents alkyl having up to 3 carbon atoms, which is optionally substituted by carboxyl, or represents a radical of the formula

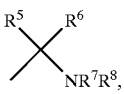

in which
$R^5$ denotes hydrogen,
$R^6$ denotes cyclopentyl, cyclohexyl or hydrogen, or denotes straight-chain or branched alkyl having up to 4 carbon atoms,
where the alkyl can optionally be substituted by cyano, methylthio, hydroxyl, mercapto, guanidyl, amino, carboxyl or $H_2N$—CO—, or the alkyl is substituted by cyclohexyl, naphthyl or phenyl which, for its part, can be substituted by fluorine. chlorine or alkoxy having up to 4 carbon atoms, or the alkyl is substituted by indolyl, imidazolyl, triazolyl, pyridyl or pyrazolyl, where the corresponding —NH functions are optionally substituted by methyl or protected by benzyloxymethylene or tert-butyloxycarbonyl (BOC), $R^7$ and $R^8$ are identical or different and denote hydrogen or tert-butyloxycarbonyl, $R^4$ represents hydrogen or a radical of the formula

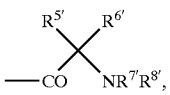

in which $R^{5'}$, $R^{6'}$, $R^{7'}$ and $R^{8'}$ have the meaning of $R^5$, $R^6$, $R^7$ and $R^8$ indicated above and are identical to or different from these, and X preferably represents hydrogen, and their stereoisomers, stereoisomeric mixtures and salts, with the exception of N-[4-[[[5-(dimethylamino)-1-naphthalenyl]sulphonyl]amino]phenyl]acetamide.

Further preferred compounds of the invention are sulphonamides of the above general formula (I), in which $R^3$ represents straight-chain or branched alkenyl having up to 4 carbon atoms, or represents straight-chain or branched alkyl having up to 5 carbon atoms, in which the alkyl carries an amino group which can be substituted by tert-butyloxycarbonyl or benzyloxycarbonyl, or the alkyl is identically or differently substituted one to 3 times by hydroxyl, cyano, fluorine, chlorine, nitro, azido, trifluoromethyl or phenyl which, for its part, can be identically or differently substituted up to 2 times by nitro, fluorine, chlorine, hydroxyl. methyl, ethyl, methoxy or ethoxy, or $R^3$ represents radicals of the formula

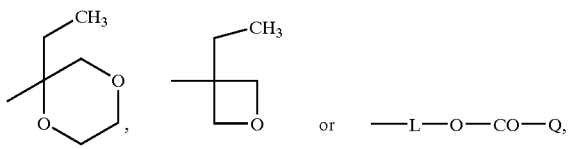

in which L or Q are as defined above, and

X preferably represents hydrogen, and their stereoisomers, stereoisomeric mixtures and salts.

Further particularly preferred compounds of the invention are sulphonamides of the above general formula (I), in which $R^1$ and $R^2$ represent straight-chain or branched alkyl having up to 4 carbon atoms, A, D, E and G represent hydrogen, $R^3$ represents straight-chain or branched alkyl having up to 5 carbon atoms, which is substituted by hydroxyl, or $R^3$ represents a radical of the formula

—L—O—CO—Q in which

L represents a straight-chain or branched alkanediyl group having up to 4 carbon atoms, Q represents a radical of the formula

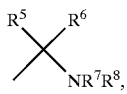

in which $R^5$ and $R^6$ denote hydrogen, and $R^7$ and $R^8$ denote hydrogen, and $R^4$ represents hydrogen, and X preferably represents hydrogen, and their stereoisomers, stereoisomeric mixtures and salts.

Very particularly preferred compounds of the invention are sulphonamides which are selected from the group of the following compounds:

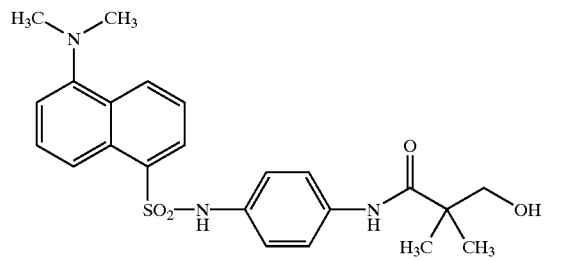

and

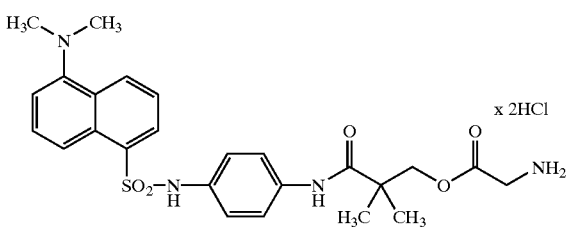

The invention furthermore relates to a process for the preparation of compounds of the above general formula (I), which is characterized in that

[A] compounds of the general formula (I)

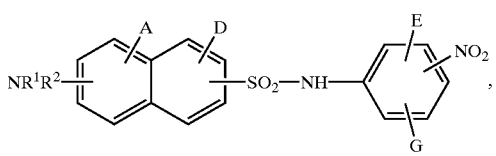

in which

A, D, E, G, $R^1$ and $R^2$ have the meaning indicated above, are first converted by catalytic hydrogenation on palladium/C or by reduction with $SnCl_2$ in inert solvents into the compounds of the general formula (III)

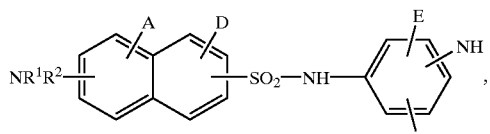 (III)

in which
A, D, E, G, $R^1$ and $R^2$ have the meaning indicated above,
and these are finally reacted with compounds of the general formula (IV)

 (IV)

in which
$R^3$ has the meaning indicated above
and
T represents hydroxyl or halogen, preferably chlorine,
in inert solvents, if appropriate in the presence of a base and/or of an auxiliary, or

[B] compounds of the general formula (V)

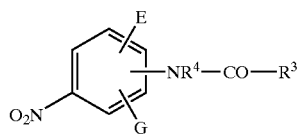 (V)

in which
E, G, $R^3$ and $R^4$ have the meaning indicated above,
are first converted as described under [A] by hydrogenation on Pd/C or by reduction with $SnCl_2$ in inert solvents into the compounds of the general formula (VI)

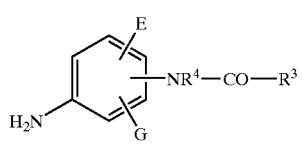 (VI)

in which
E, G, $R^3$ and $R^4$ have the meaning indicated above,
and these are finally reacted with compounds of the general formula (VII)

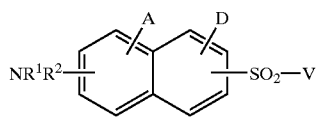 (VII)

in which
A, D, $R^1$ and $R^2$ have the meaning indicated above
and
V represents halogen, preferably chlorine,
in inert solvents, if appropriate in the presence of a base and/or of an auxiliary, or
[C] if $R^3$ and/or $R^{3'}$ represent a radical of the formula —L—O—CO—Q, compounds of the general formula (Ia)

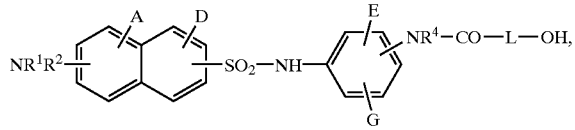 (Ia)

in which
$R^1$, $R^2$, $R^4$, A, D, E, G and L have the meaning indicated above,
are reacted with amino acid residues of the general formula (III)

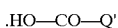 (VIII)

in which
Q' has the meaning of Q indicated above, where one of the terminal radicals on the nitrogen, mentioned there, represents one of the abovementioned protective groups, preferably tert-butyloxycarbonyl,
if appropriate with activation of the carboxylic acid according to customary methods, in inert solvents and in the presence of a base and of an auxiliary,
and finally the protective group is removed according to the methods customary in peptide chemistry,
and in the case in which X, $R^4 \neq H$ is reacted with 2 or more equivalents of the compounds of the general formula (VIII),
if appropriate the stereoisomers are separated according to methods known per se and if appropriate the free bases are converted into the salts or the salts are converted into the free bases.

The invention furthermore relates to sulphonamides of the above general formula (I) for the prophylaxis or treatment of diseases.

The invention furthermore relates to the use of sulphonamides of the above general formula (I) for the production of medicaments, in particular medicaments for the control of viral disorders and preferably medicaments for the control of cytomegalovirus.

The invention finally relates to medicaments comprising sulphonamides of the above general formula (I).

The substances according to the invention can also be present as salts. In the context of the invention physiologically acceptable salts are preferred.

Physiologically acceptable salts can be salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthalenedisulphonic acid.

Physiologically acceptable salts can also be metal or ammonium salts of the compounds according to the invention. Those particularly preferred are, for example, sodium, potassium, magnesium or calcium salts, as well as ammonium salts which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

By the term "alkanediyl group", hydrocarbon groups are indicated here which are linked to further radicals in two positions. Preferably, these linkage sites are located on different carbon atoms.

Examples of alkanediyl groups are: —CH$_2$—CH$_2$—, —CH$_2$—CH$_2$—CH$_2$—, —C(CH$_3$)$_2$—CH$_2$—, —CH(CH$_3$)—CH$_2$—, —C(CH$_3$)$_2$—CH$_2$—CH$_2$—, —CH(CH$_3$)—CH$_2$—CH$_2$— etc.

Amino protective groups in the context of the invention are the customary amino protective groups used in peptide chemistry.

These preferably include: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro4,5-dimethoxybenzyloxycarbonyl, methoxycarbonyl, ethoxycarbonyl, propoxy-carbonyl, isopropoxycarbonyl, butoxycarbonyl, isobutoxycarbonyl, tert-butoxycarbonyl, allyloxycarbonyl, vinyloxycarbonyl, 2-nitrobenzyloxycarbonyl, 3,4,5-trimethoxybenzyloxycarbonyl, cyclohexoxycarbonyl, 1,1-dimethylethoxy-carbonyl, adamantylcarbonyl, phthaloyl, 2,2,2-trichloroethoxycarbonyl, 2,2,2-trichloro-tert-butoxycarbonyl, menthyloxycarbonyl, phenoxycarbonyl, 4-nitro-phenoxycarbonyl, fluorenyl-9-methoxycarbonyl, formyl, acetyl, propionyl, pivaloyl, 2-chloroacetyl; 2-bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dinitroberizyl or 4-nitrophenyl.

The compounds of the general formula (I) according to the invention can occur in different stereochemical forms, which either behave as image and mirror image (enantiomers), or which do not behave as image and mirror image (diastereomers). The invention relates both to the antipodes and to the racemic forms as well as the diastereomer mixtures. Like the diastereomers, the racemic forms can be separated into the stereoisomerically uniform constituents in a known manner.

With respect to the amino acid residue, the compounds of the general formula (I) according to the invention can be present either in the D or L form, and the R or S configuration. The invention includes the optical antipodes as well as the isomer mixtures or racemates.

In the context of the invention, the compounds of the general formula (I) according to the invention can be bonded to the naphthyl structure in the α- or β-position in relation to the —SO$_2$—NX-group and the NH—CO—R$^3$ group can be linked to the phenyl ring in the o-, m- or p-position.

(A)

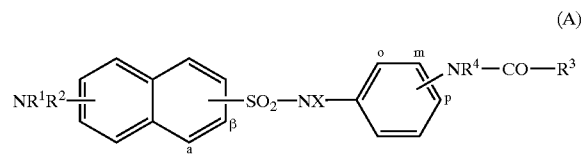

Preferably, the —SO$_2$—NX group is bonded to the naphthyl structure in the in α- or β-position and the —NR$^4$—CO—R$^3$ group is bonded to the phenyl radical in the m- or p-position.

Particularly preferably, the —SO$_2$—NX group is bonded to the naphthyl structure in the α-position and the —NR$^4$—CO—R$^3$ group is linked to the phenyl radical in he p-position.

Particularly preferred compounds are shown in Table A:

TABLE A

Structure

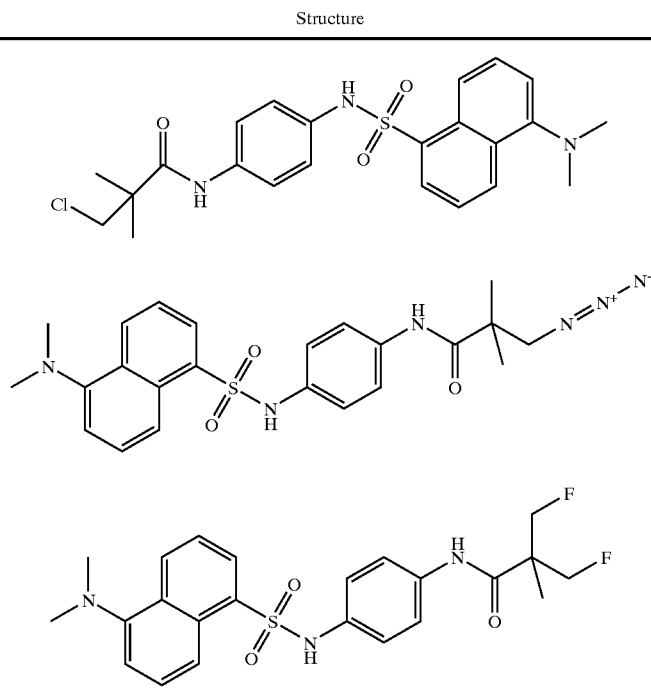

TABLE A-continued
Structure
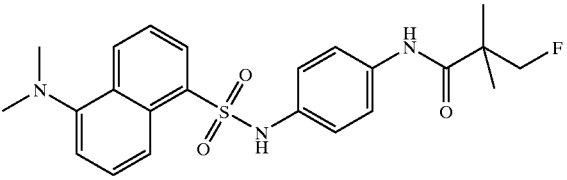
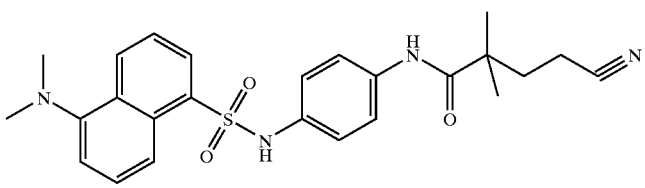
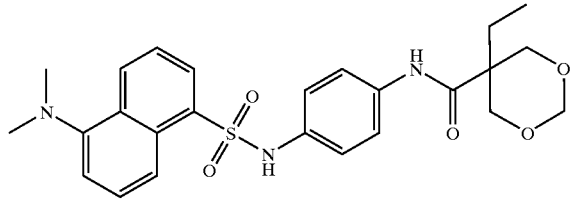
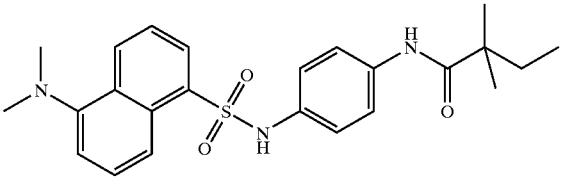
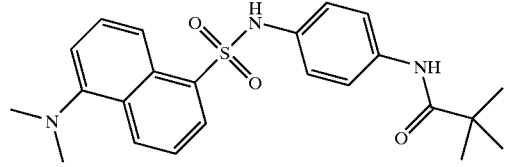
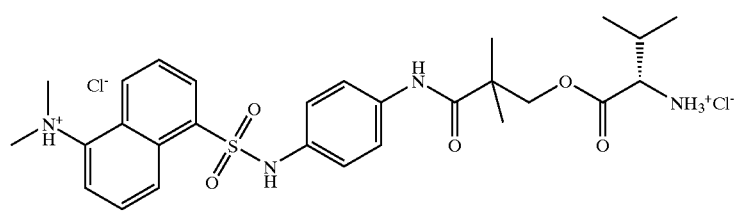
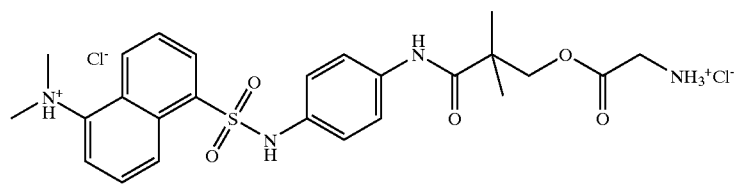

TABLE A-continued
Structure
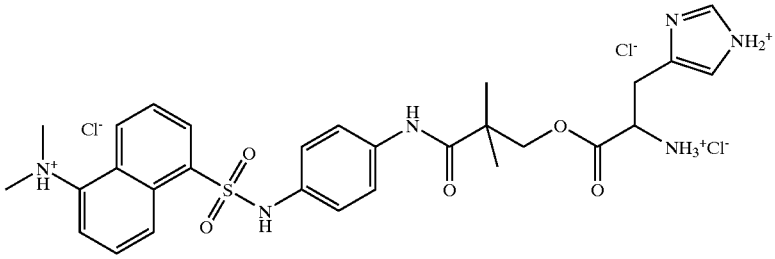
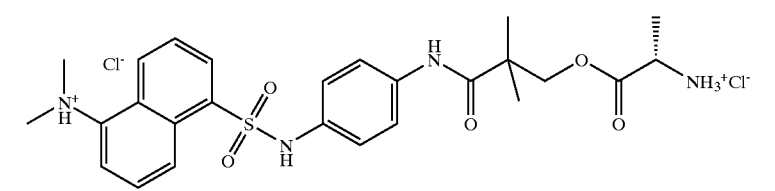
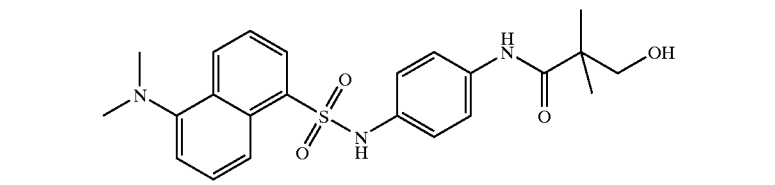
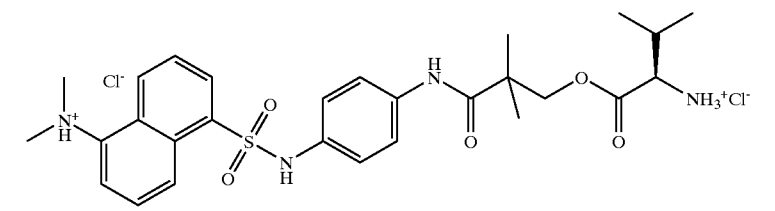
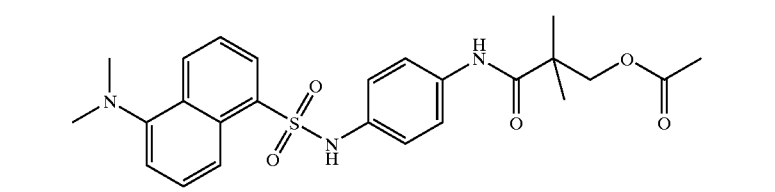
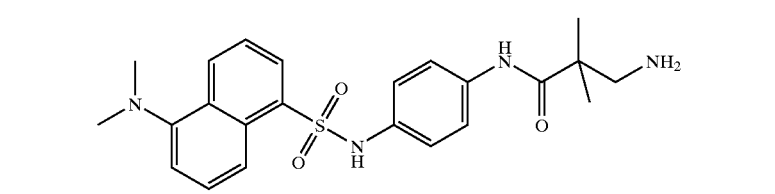
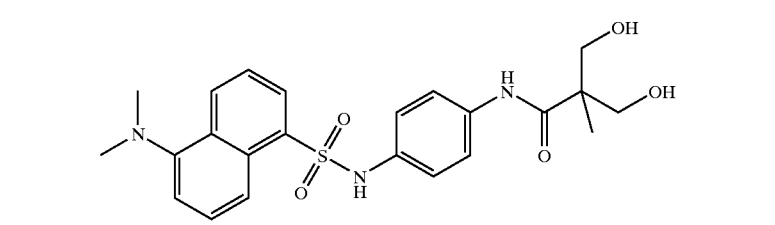

TABLE A-continued

Structure

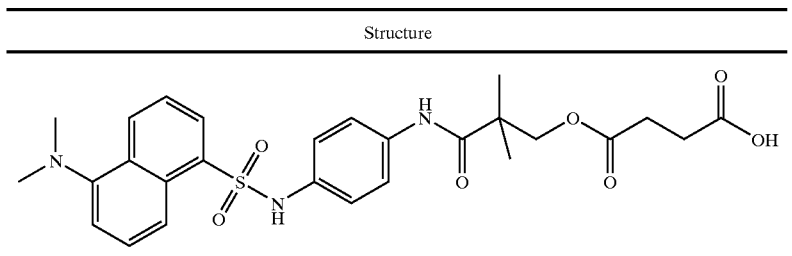

The particularly preferred compounds shown in Table A can be present in the form of the free base, as pharmaceutically acceptable salts, in particular hydrochlorides, or optionally as zwitterions.

The compounds of the general formula (I) according to the invention can be prepared by a process in which

[A] compounds of the general formula (II)

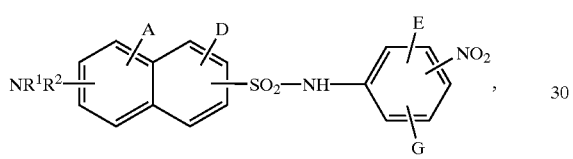

in which
A, D, E, G, $R^1$ and $R^2$ have the meaning indicated above,
are first converted by catalytic hydrogenation on palladium/C or by reduction with $SnCl_2$ in inert solvents into the compounds of the general formula (III)

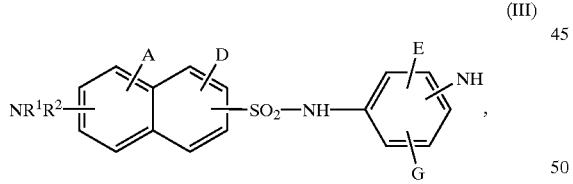

in which
A, D, E, G, $R^1$ and $R^2$ have the meaning indicated above,
and these are finally reacted with compounds of the general formula (IV)

in which
$R^3$ has the meaning indicated above
and
T represents hydroxyl or halogen, preferably chlorine,
in inert solvents, if appropriate in the presence of a base and/or of an auxiliary, or

[B] compounds of the general formula (V)

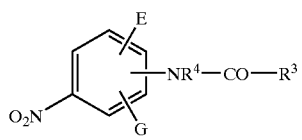

in which
E, G, $R^3$ and $R^4$ have the meaning indicated above,
are first converted as described under [A] by hydrogenation on Pd/C or by reduction with $SnCl_2$ in inert solvents into the compounds of the general formula (VI)

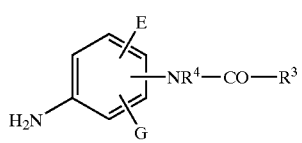

in which
E, G, $R^3$ and $R^4$ have the meaning indicated above,
and these are finally reacted with compounds of the general formula (VII)

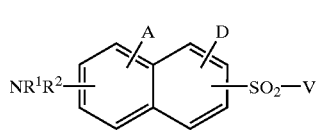

in which
A, D, $R^1$ and $R^2$ have the meaning indicated above
and
V represents halogen, preferably chlorine,
in inert solvents, if appropriate in the presence of a base and/or of an auxiliary, or

[C] if $R^3$ and/or $R^3$ represent a radical of the formula —L—O—CO—Q, compounds of the general formula (Ia)

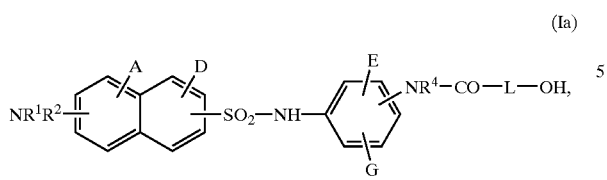

in which
R¹, R², R⁴, A, D, E, G and L have the meaning indicated above,
are reacted with amino acid residues of the general formula (VIII)

HO—CO—Q'  (VIII)

in which
Q' has the meaning of Q indicated above, where one of the terminal radicals on the nitrogen, mentioned there, represents one of the abovementioned protective groups, preferably tert-butyloxycarbonyl,
if appropriate with activation of the carboxylic acid according to customary methods, in inert solvents and in the presence of a base and of an auxiliary,
and finally the protective group is removed according to the methods customary in peptide chemistry,
and in the case in which X, R⁴≠H is reacted with 2 or more equivalents of the compounds of the general formula (VIII), The process according to the invention can be illustrated by way of example by the following reaction schemes:

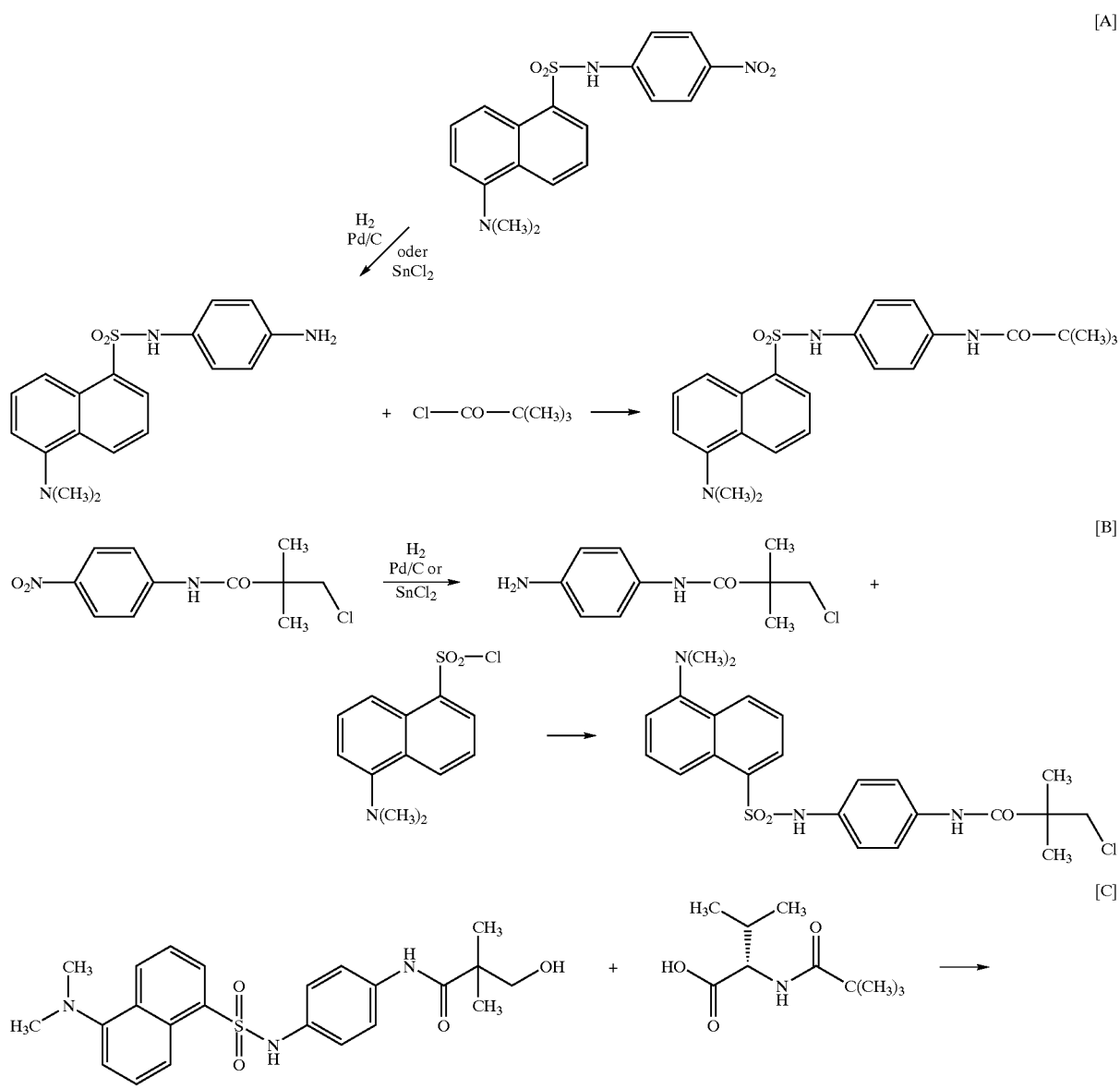

-continued

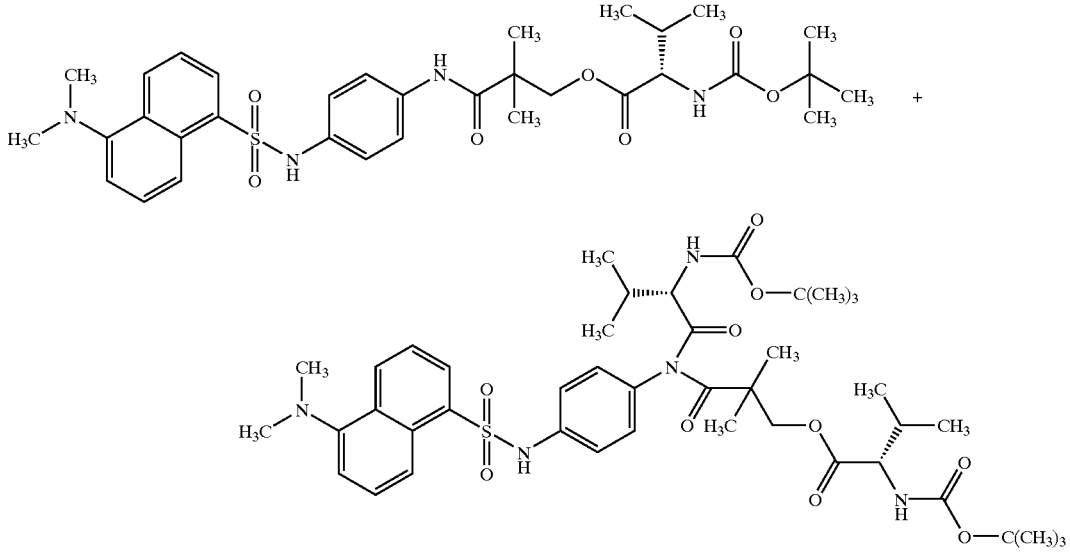

Suitable solvents for all process steps are the customary inert solvents which do not change under the reaction conditions. These preferably include organic solvents such as ethers, e.g. diethyl ether, glycol mono- or dimethyl ether, dioxane or tetrahydro furan, or hydrocarbons such as benzene, toluene, xylene, cyclohexane or petroleum fractions or halogenohydrocarbons such as methylene chloride, chloroform, carbon tetrachloride, or dimethyl sulphoxide, dimethylformamide, hexamethylphosphoramide, ethyl acetate, pyridine, triethylamine or picoline. It is also possible to use mixtures of the solvents mentioned, if appropriate also with water. Methylene chloride, tetrahydrofuran, pyridine and dioxane are particularly preferred.

Suitable bases are organic amines, in particular trialkyl ($C_1$–$C_6$)amines such as, for example, triethylamine or heterocycles such as pyridine, methylpiperidine, piperidine or N-methylmorpholine. Pyridine, triethylamine and N-methylmorpholine are preferred.

In general, the bases are employed in an amount from 0.1 mol to 5 mol, preferably from 1 mol to 3 mol, in each case relative to I mol of the compounds of the general formulae (III) and (IV).

Suitable auxiliaries are carbodiimides such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate or benzotriazolyloxy-tris(dimethylamino)phosphonium hexafluorophosphate or diphenyl phosphora-midate or methanesulphonyl chloride, if appropriate in the presence of bases such as triethylamine or N-ethylmorpholine or N-methylpiperidine or dicyclohexylcarbodiimide and N-hydroxysuccinimide.

The reactions can be carried out at normal pressure, but also at elevated or reduced pressure (e.g. 0.5 to 3 bar). In general, they are carried out at normal pressure.

The reactions are carried out in a temperature range from 0° C. to 100° C., preferably at 0° C. to 30° C. and at normal pressure.

In general, the reductions can be carried out by means of hydrogen in water or in inert organic solvents such as alcohols, ethers or halogenohydrocarbons, or their mixtures, using catalysts such as Raney nickel, palladium, palladium on animal charcoal or platinum, or using hydrides such as $SnCl_2$, or boranes in inert solvents, if appropriate in the presence of a catalyst. Palladium on animal charcoal or $SnCl_2$ is preferred.

The reaction can be carried out at normal, elevated or at reduced pressure (e.g. 0.5 to 5 bar). In general, it is carried out at normal pressure.

In general, the reductions are carried out in a temperature range from 0° C. to +60° C., preferably at +10° C. to +40° C.

Suitable solvents for the acylation are customary organic solvents which do not change under the reaction conditions. These preferably include ethers, such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichlorethylene or chlorobenzene, or ethyl acetate, or triethylamine, pyridine, dimethyl sulphoxide, dimethylformamide, hexamethylphosphoramide, acetonitrile, acetone or nitromethane. It is also possible to use mixtures of the solvents mentioned. Dichloromethane and pyridine are preferred.

The acylation is carried out in the abovementioned solvents at temperatures from 0° C. to +150° C., preferably at room temperature to +100° C. and at normal pressure.

Suitable solvents for process [C] are customary organic solvents which do not change under the reaction conditions. These preferably include organic solvents such as alcohols, e.g. methanol, ethanol or n-propanol, ethers, for example, diethyl ether, glycol mono- or -dimethyl ether, dioxane or tetrahydrofuran, or hydrocarbons such as benzene, toluene, xylene, cyclohexane or petroleum fractions or halogenohydrocarbons such as methylene chloride, dichloroethane (DCE), chloroform, carbon tetrachloride, or dimethyl sulphoxide, dimethylformamide, hexamethylphosphoramide, ethyl acetate, pyridine, triethylamine or picoline. It is also possible to use mixtures of the solvents mentioned. Dichloromethane, dichloroethane, dimethylformamide and n-propanol are particularly preferred.

Auxiliaries employed for the respective peptide couplings are preferably condensing agents, which can also be bases, in particular if the carboxyl group is present activated as an anhydride. Preferably, the customary condensing agents are employed here such as carbodiimides, e.g. N,N'-diethyl-, N'-dipropyl-, N,N'-diisopropyl-, N,N'-dicyclohexylcarbodiimide, N-(3-dimethylaminoisopropyl)-N'-ethylcarbodiimide hydrochloride, or carbonyl compounds such as carbonyldiimidazole, or 1,2-oxazolium compounds such as 2-ethyl-5-phenyl-1,2-oxazolium-3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or benzotriazolyloxy-tris(dimethylamino)phosphonium hexafluoro-phosphate, or 1-hydroxybenzotriazole and as bases, alkali metal carbonates, e.g. sodium or potassium carbonate, or sodium or potassium hydrogencarbonate, or organic bases such as trialkylamines, e.g. triethylamine, N-ethylmorpholine, N-methylpiperidine or diisopropylethylamine. Dicyclohexyl-carbodiimide, N-methylmorpholine and 1-hydroxybenzotriazole are particularly preferred.

The amino protective group is removed in a manner known per se under acidic or basic conditions, or reductively by catalytic hydrogenation, for example using Pd/C in organic solvents such as ethers, e.g. tetrahydrofuran or dioxane, or alcohols, e.g. methanol, ethanol or isopropanol.

The amino protective groups can also be removed by customary methods using acids, such as, for example, hydrochloric acid or trifluoroacetic acid.

In general, the reactions are carried out in a temperature range from −20° C. to +80° C., preferably from 0° C. to +60° C.

In general, the reaction is carried out at normal pressure. However, it is also possible to work at reduced pressure or at elevated pressure (e.g. from 0.5 to 5 bar).

The compounds of the general formula (VIII) are known.

The compounds of the general formula (Ia) are new and can be prepared as shown above under processes [A] and [B].

The compounds of the general formulae (II). (III), (IV), (V), (VI) and (VII) are known per se or can be prepared by methods known from the literature.

The present invention additionally includes the use of N-[4-[[[5-(dimethylamino)-1-naphthalenyl]sulphonyl]amino]phenyl]acetamide as an antiviral agent, in particular against cytomegaloviruses.

The compounds of the general formulae (I) and (Ia) according to the invention exhibit an unforeseeable surprising spectrum of action. They exhibit an antiviral action against representatives of the herpesviridae group, particularly against human cytomegalovirus (HCMV). They are thus suitable for the treatment and prophylaxis of disorders which are caused by herpes viruses, in particular disorders which are caused by human cytomegalovirus (HCMV).

The anti-HCMV action was determined in a screening test system in 96-well microtitre plates with the aid of human embryonic lung fibroblast (HELF) cell cultures. The effect of the substances on the spread of the cytopathogenic effect was determined in comparison with the reference substance ganciclovir (Cymevene® sodium), a clinically approved anti-HCMV chemotherapeutic.

The substances dissolved (50 mM) in DMSO (dimethyl sulphoxide) are investigated on microtitre plates (96-well) in duplicate determinations (4 substances/plate). Toxic and cytostatic substance effects are additionally detected at the same time. After the appropriate substance dilutions (1:2) on the microtitre plate, a suspension of 50–100 HCMV-infected HELF cells and $30 \times 1^{05}$ non-infected HELF cells in Eagle's MEM with 10% foetal calf serum is added to each well, and the plates are incubated at 37° C. in a $CO_2$ incubator for several days. After this time, the cell lawn in the sub-stance-free virus controls, starting from 50–100 infectious centres, is completely destroyed by the cytopathogenic effect of the HCMV (100% CPE). After staining with Neutral Red and fixing with formalin/methanol, the plates are assessed with the aid of a projection microscope (plaque-viewer). The results are summarized for some compounds in the following table:

TABLE

| Ex. No. | HCMV $EC_{50}$ |
|---------|----------------|
| 1       | 0.16           |
| 2       | 0.27           |
| 13      | 0.064          |
| 16      | 0.028          |
| 24      | 0.88           |
| 25      | 0.64           |

It has now been found that the compounds according to the invention inhibit the replication of the HCMV in HELF cells in concentrations which are in some cases 10- to 50-fold lower than Cymeven® sodium and have a selectivity index which is several times higher.

The compounds according to the invention are thus valuable active substances for the treatment and prophylaxis of disorders which are caused by human cytomegalovirus.

Examples of indication areas which may be mentioned are:

1) Treatment and prophylaxis of HCMV infections in AIDS patients (retinitis, pneumonitis, gastrointestinal infections).
2) Treatment and prophylaxis of cytomegalovirus infections in bone marrow and organ transplant patients who suffer from HCMV pneumonitis or encephalitis and also from gastrointestinal and systemic HCMV infections, often with life-threatening consequences.
3) Treatment and prophylaxis of HCMV infections in new-born children and infants.
4) Treatment of an acute HCMV infection in pregnant women.

In vivo Action

Animals 5 week-old male mice, NOD/LtSz-Prkdc(scid)/J strain, were obtained from a commercial breeder (The Jackson Lab., Bar Harbor). The animals were kept in isolators under sterile conditions (including litter and feed).

Virus/infection

Murine cytomegalovirus (MCMV), Smith strain, was passaged in vivo (BALB/c) and purified by means of fractional centrifugation. The titre was investigated with the aid of a plaque assay for primary embryonic mouse fibroblasts. The mice were infected with a dose of $5 \times 10^5$ pfu in a total volume of 0.2 ml intraperitoneally. This dose leads to death in 100% of the infected animals after about 11 days.

Treatment/assessment 24 hours after infection, the mice were treated orally with substance twice daily (morning and evening) over a period of 8 days. The dose was 25 mg/kg of body mass, the administration volume 10 ml/kg of body mass. The substances were formulated in the form of a 0.5% strength Tylose suspension. 16 hours after the last substance administration, the animals were painlessly killed and the salivary gland, liver and kidney were removed.

Genomic DNA was purified from 25 mg of the tissue by means of phenol/chloroform extraction. The DNA was quantified photometrically and with the aid of the formula $OD_{260} \times 50 = mg/ml$.

The purity of the DNA was checked by means of the quotient $OD_{260}/OD_{280}$ and the DNA was then adjusted to pH=8.0 using tris-EDTA.

The MCMV-DNA was quantified by means of DNA dot blot hybridization. The probe used was a digoxygenin-labelled (Boehringer-Mannheim, also the buffers mentioned, if not described otherwise) 1.2 kb fragment from the MCMV region, Smith, HindIII J. The signals were detected by means of chemoluminescence. For this purpose, the membrane was washed for 3 minutes in 1×digoxygenin-wash buffer 1. Following this, the filters were incubated at room temperature for 30 minutes in 1×digoxygenin blocking solution with shaking. The filters were then incubated with the anti-DIG alkaline phosphatase conjugate solution (1:20000 in 1×digoxygenin blocking solution) for 30 minutes in 20 ml/100 cm² membrane. 2 washing steps with 1×digoxygenin-wash buffer lasting 15 minutes each then took place. A 5 minute equilibration of the filters in 1×digoxygenin detection buffer and detection by means of 1 ml/100 cm² membrane surface area of 1:100 diluted CDP star solution followed. After streaking out the CDP star solution and incubation for 5 minutes in a dark box, chemoluminescence was detected or assessment was carried out by means of X-ray film (Kodak) or Lumilmager (Boehringer Mannheim).

All results were confirmed statistically (variance analysis by means of statistics StatSoft Inc.).

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration from approximately 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifying agents and/or dispersing agents, it being possible, for example, if water is used as a diluent, optionally to use organic solvents as auxiliary solvents.

Administration is carried out in a customary manner, preferably orally, parenterally or topically, in particular perlingually, intravenously or intravitreally, if appropriate as a depot in an implant.

In the case of parenteral administration, solutions of the active compounds using suitable liquid carrier materials can be employed.

In general it has proved advantageous in the case of intravenous administration to administer amounts from approximately 0.001 to 10 mg/kg, preferably approximately 0.01 to 5 mg/kg, of body weight to achieve effective results, and in the case of oral administration the dose is approximately 0.01 to 25 mg/kg, preferably 0.1 to 10 mg/kg, of body weight.

In spite of this, if appropriate it may be necessary to depart from the amounts mentioned, mainly depending on the body weight or on the type of administration route, on individual behaviour towards the medicament, the manner of its formulation and the time or interval at which administration takes place. Thus in some cases it may be adequate to manage with less than the abovementioned minimum amount, while in other cases the upper limit mentioned must be exceeded. In the case of the administration of relatively large amounts, it may be advisable to divide these into several individual administrations over the course of the day.

If appropriate, it may be useful to combine the compounds according to the invention with other active substances.

Eluent Mixtures:

| | |
|---|---|
| A | Methylene chloride:methanol 100:0 |
| B | Methylene chloride:methanol 100:1 |
| C | Methylene chloride:methanol 100:2 |
| D | Methylene chloride:methanol 100:3 |
| E | Methylene chloride:methanol 100:5 |
| F | Methylene chloride:methanol 10:1 |
| G | Methylene chloride:methanol:ammonia 10:1:0.1 |
| H | Methylene chloride:cyclohexane 1:1 |
| I | Cyclohexane:ethyl acetate 95:5 |
| K | Cyclohexane:ethyl acetate 90:10 |
| L | Cyclohexane:ethyl acetate 85:15 |
| M | Cyclohexane:ethyl acetate 80:20 |
| N | Cyclohexane:ethyl acetate 75:25 |
| O | Cyclohexane:ethyl acetate 70:30 |
| P | Cyclohexane:ethyl acetate 60:40 |
| Q | Cyclohexane:ethyl acetate 50:50 |
| R | Cyclohexane:ethyl acetate 40:60 |
| S | Cyclohexane:ethyl acetate 30:70 |
| T | Butanol:glacial acetic acid:water 4:1:1 |
| U | Methylene chloride:methanol 9:1 |
| V | Acetonitrile:water 9:1 |
| W | Cyclohexane:ethyl acetate 1:10 |
| X | Acetonitrile:water 95:5 |
| Y | Methylene chloride:methanol 95:5 |
| Z | Petroleum ether:ethyl acetate 1:1 |
| ZA | Petroleum ether:ethyl acetate 1:2 |
| ZB | Petroleum ether:ethyl acetate 1:3 |

STARTING COMPOUNDS

EXAMPLE I

4-[5-N,N-Dimethylaminonaphthyl-1-sulphonamino]nitrobenzene

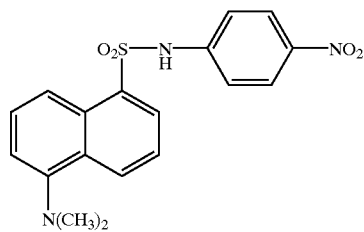

51.2 g (0.37 mol) of p-nitroaniline are introduced into 700 ml of pyridine under argon and with ice-bath cooling and are treated in portions with 100 g (0.37 mol) of dansyl chloride. The mixture is then stirred at room temperature overnight. TLC checking in petroleum ether (PE)/ethyl acetate (EA) 7:3 indicates a homogeneous reaction. For working-up, the reaction mixture is freed from pyridine in vacuo and the residue is taken up in 1 N sodium hydroxide solution. The aqueous phase is freed from residual pyridine again in vacuo and then adjusted to pH 4 using hydrochloric acid. The precipitated product is filtered off with suction. After drying in a circulating air oven at 60° C., 82 g (60%) of the sulphonamide are obtained as a lemon-yellow solid.

MS (CI, $NH_3$, m/e): 372 ([M+H]⁺, 100%).

¹H-NMR (200 MHz, DMSO-$d_6$, δ/ppm): 8.46 (d, J=9.0 Hz; 1H), 8.40–8.31 (m; 2H), 8.05 (d, J=10 Hz; 2H), 7.65 (dt, $J_1$=7.5 Hz, $J_2$=5 Hz; 2H), 7.28–7.18 (m; 3H), 2.80 (s; 6H).

EXAMPLE II

4-[5-N,N-Dimethylaminonaphthyl-1-sulphonylamino]aniline

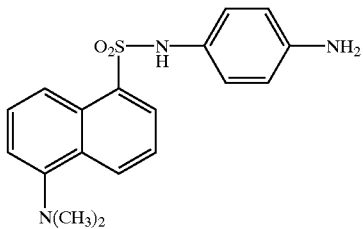

63 g (0.17 mol) of the compound from Example I are dissolved in 400 ml of ethanol, treated with 1.5 g of 10% Pd on active carbon and hydrogenated at 3 bar of hydrogen for 25 h. TLC checking petroleum ether (PE)/ethyl acetate (EA) 1:1 ($R_f$=0.28) indicates complete reaction. For working-up, the catalyst is filtered off and the filtrate is freed from the solvent in vacuo. The hard foam thus obtained is dissolved in 1 N sulphuric acid and then extracted with ether. It is rendered neutral using 2.5 N sodium hydroxide solution and the precipitate is filtered off with suction. The product is dried at 60° C. in a circulating air oven. 50 g (86%) of the amine are obtained as a white solid.

$R_f$=0.29 (E).

MS (CI, $NH_3$, m/e): 342 ([M+H]$^+$, 100%).

$^1$H-NMR (200 MHz, DMSO-d6, δ/ppm): 9.80 (s; 1H), 8.42 (d, J=8.0 Hz; 1H), 8.38 (d, J=8.0 Hz; 1H), 8.00 (d, J=7.5 Hz; 1H), 7.60 (t, J=7.5 Hz; 1H), 7.54 (t, J=7.5 Hz; 1H), 7.25 (d, J=7.5 Hz; 1H), 6.60 (d, J=9.0 Hz; 2H), 6.40 (d, J=9.0 Hz; 2H), 4.90 (s; 2H), 2.80 (s; 6H).

EXAMPLE III

N-(4-Nitrophenyl)pivaloylamide

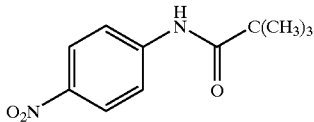

20 g (0.14 mol) of 4-nitroaniline are dissolved in 400 ml of methylene chloride and 100 ml of dioxane in a 1 l three-necked flask. The solution is then treated with 23.4 ml of pyridine. 19.2 g (0.16 mol) of pivaloyl chloride are added dropwise with ice-cooling. The mixture is stirred at RT for 24 h. It is then extracted 3× by shaking with 200 ml of water and the organic phase is dried using sodium sulphate. The organic phase is concentrated in a rotary evaporator and the residue is stirred well in 100 ml of diisopropyl ether for 2 h, filtered off with suction, washed with diisopropyl ether and pentane and dried.

Yield: 30 g (93% of theory).

EXAMPLE IV

N-((4-Aminophenyl)pivaloylamide

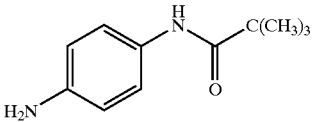

25 g (0.11 mol) of the compound from Example III are dissolved in 500 ml of dioxane with stirring in a 1l round-bottomed flask. The solution is then covered with a layer of argon and 5 g of 10% Pd on active carbon are added. It is hydrogenated at room temperature under normal pressure for 20 h. The catalyst is filtered off through kieselguhr and the mother liquor is concentrated in a rotary evaporator. The residue is stirred well in 200 ml of heptane for 2 h, filtered off with suction and washed with heptane, and the crystals are dried.

Yield: 19.6 g (90.6%).

PREPARATION EXAMPLES

EXAMPLE 1

N-[4-(5-N,N-Dimethylaminonaphthyl-1-sulphonylamino]phenyl]-2,2-dimethylpropionamide

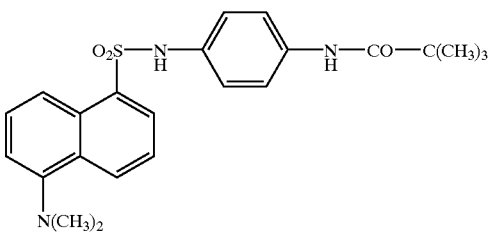

17.8 g (0.09 mmol) of the compound from Example IV are introduced under argon into pyridine and 25 g (0.09 mol) of dansyl chloride are added in portions. The mixture is then stirred at room temperature for 18 h (TLC checking PE:EA 7:3). For working-up, the pyridine is removed in vacuo, and the residue is taken up in dioxane and precipitated again using water. Since the product is initially obtained as an oil, it is separated from the aqueous solvent, the oil is stirred with ether and the crystalline precipitate is filtered off with suction. A slightly yellowish solid is obtained.

M.p.: 174° C.

EXAMPLE 2

N-[4-(5-(N,N-Dimethylamino)naphthyl-1-sulphonylamino)phenyl]-3-hydroxy-2,2-dimethylpropionamide

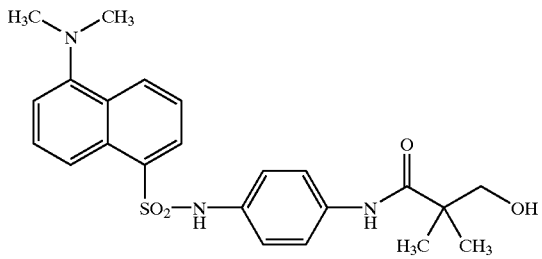

50 g (0.15 mol) of the compound from Example II are treated with 203 ml (1.46 mol) of triethylamine and 51.9 g (0.44 mol) of 3-hydroxy-2,2-dimethylpropionic acid in 800 ml of methylene chloride. 200 ml of a 1.7 M solution of n-propanephosphonic anhydride in ethyl acetate are added dropwise with cooling in the course of 30 min such that the internal temperature does not exceed 15° C. The mixture is subsequently stirred overnight at room temperature. TLC checking in methylene chloride/methanol 100:5 ($R_f$=0.29) indicates complete reaction. For working-up, the mixture is diluted with 800 ml of methylene chloride, and washed 4 times with water and once with dilute acetic acid. After drying over sodium sulphate, it is freed from the solvent in vacuo. The residual hard foam is purified by means of a silica gel column (eluents: D, E, F, G). The hard foam thus obtained is crystallized from toluene. 33 g (51%) of the amide are thus obtained as a white solid.

MS (CI, $NH_3$, m/e): 442 ([M+H]$^+$, 100%).

$^1$H-NMR (200 MHz, DMSO-$d_6$, δ/ppm): 10.46 (s; 1H), 9.10 (s; 1H), 8.40 (t broad, J=7.5 Hz; 2H), 8.14 (d, J=7.5 Hz; 1H), 7.62 (t, J=7.5 Hz; 1H), 7.55 (t, J=7.5 Hz; 1H), 7.36 (d, J=10.0 Hz; 2H), 7.24 (d, J=7.5 Hz; 1H), 6.92 (d, J=10.0 Hz; 2H), 5.04 (t, J=5.0 Hz; 1H), 3.42 (d, J=5.0 Hz; 2H), 2.80 (s; 6H), 1.07 (s; 6H).

EXAMPLE 3 AND EXAMPLE 4

N-[4-(5-N,N-Dimethylaminonaphthyl-1-sulphonylamino)phenyl]-3-((2S)-2-(N-tert-butyloxycarbonylamino)-2-isopropylacetoxy)-2,2-dimethylpropionamide (Example 3) and N-[4-(5-N,N-dimethylaminonaphthyl-1-sulphonylamino)phenyl]-N-[(2S)-2-(N-tert-butyloxycarbonylamino)-2-isopropylacetyl]-3-(2S)-2-(N-tert-butyloxycarbonylamino)-2-isopropylacetoxy)-2,2-dimethylpropionamide (Example 4)

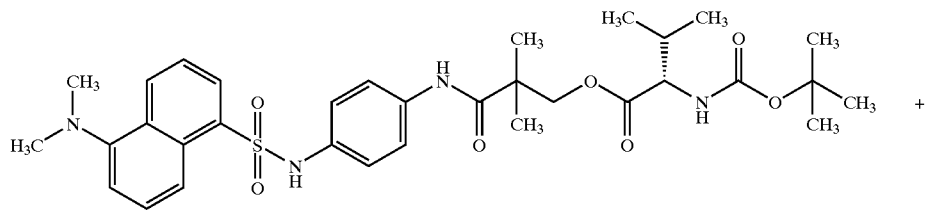

(Example 3)

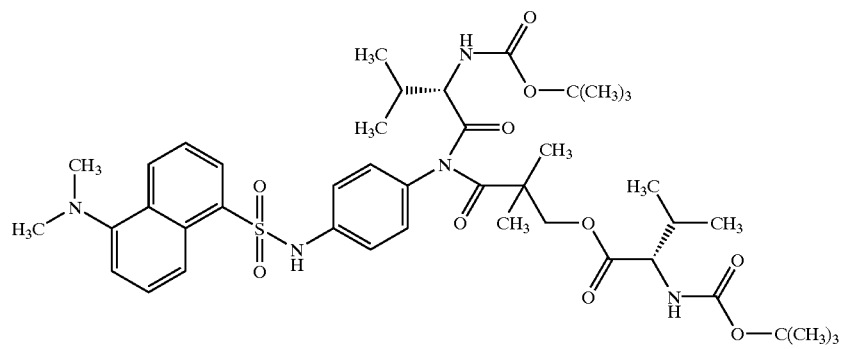

(Example 4)

10.0 g (0.02 mol) of the compound from Example 2, 6.4 g (0.03 mol) of N-Boc-L-valine and 1.1 g (0.01 mol) of dimethylaminopyridine are introduced into 170 ml of methylene chloride and 6.1 g (0.03 mol) of EDC are added. The mixture is then stirred overnight at room temperature. It is then diluted with ethyl acetate, extracted twice with saturated NaHCO$_3$ solution and dried. Purification is carried out by means of a silica gel column using petroleum ether/ethyl acetate 2:1.

EXAMPLE 3

Yield: 10.8 g (74.4%) R$_f$=0.55 (Z).

EXAMPLE 4

Yield: 1.7 g (8.9%) R$_f$=0.65 (Z).

EXAMPLE 5

N-[4-(5-N,N-Dimethylaminonaphthyl-1-sulphonylamino)phenyl]-3-((2S)-2-amino-2-isopropylacetoxy)-2,2-dimethylpropionamide Dihydrochloride

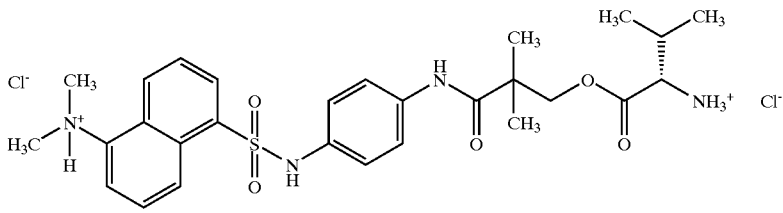

10.5 g (0.02 mol) of the compound from Example 3 are treated with 200 ml of 4 N HCl in dioxane and stirred for 4 h. The mixture is then concentrated in a rotary evaporator, the residue is dissolved twice in 100 ml of water and the solution is again concentrated in a rotary evaporator. It is then treated twice with 100 ml of acetonitrile, concentrated in a rotary evaporator and treated twice with ether and again concentrated in a rotary evaporator. It is dried overnight on an oil pump.

9.7 g (96%) of a pale yellow powder are obtained (m.p. 130° C., dec.).

EXAMPLE 6

N-[4-(5-N,N-Dimethylaminonaphthyl-1-sulphonylamino)phenyl]-3-(2-(N-tert-butyloxycarbonylamino)-2-acetoxy)-2,2-dimethylpropionamide

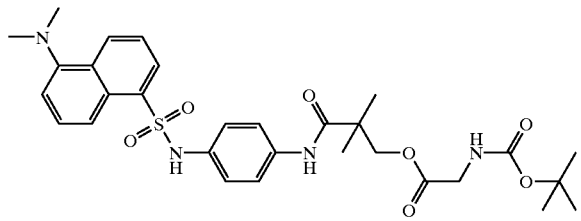

14.3 g (0.08 mol) of BOC-glycine are introduced into 300 ml of methylene chloride at room temperature, and the mixture is treated with 13.2 g (0.08 mol) of carbonyldiimidazole and stirred at this temperature for 2 h. After TLC checking, 30.0 g (0.07 mol) of Example 2 are added and the mixture is subsequently stirred overnight at room temperature.

For working-up, it is diluted with 500 ml of methylene chloride, and washed 2× with 300 ml of 0.01 N sulphuric acid and 1× with water. After drying over sodium sulphate, it is concentrated in a rotary evaporator and a greenish hard foam is obtained, which is crystallized from toluene.

43.0 g (88% of theory) of Example 43 are obtained as greenish crystals.

MS (CI, NH$_3$, m/e): 616 ([M+H]$^+$, 100%).

$^1$H-NMR (200 MHz, DMSO-d$_6$, δ/ppm): 10.50 (s; 1H), 9.12 (s; 1H), 8.40 (t, J=8.0 Hz; 2H), 8.14 (d, J=8.0 Hz; 1H), 7.68–7.52 (m; 2H), 7.35 (d, J=10.0 Hz; 2H), 7.26 (d, J=8.0 Hz; 1H), 6.94 (d, J=10.0 Hz; 2H), 4.12 (s; 2H), 3.62 (d, J=6.0 Hz; 2H), 2.80 (s; 6H), 1.32 (s; 9H) 1.15 (s; 6H).

EXAMPLE 7

N-[4-(5-N,N-Dimethylaminonaphthyl-1-sulphonylamino)phenyl]-3-(2-aminoacetoxy)-2,2-dimethylpropionamide Hydrochloride

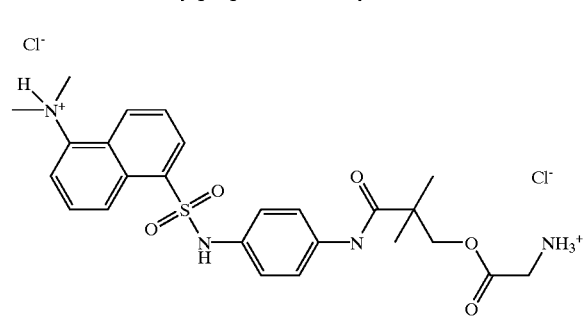

39.5 g (0.07 mol) of the compound from Example 6 are introduced into 200 ml of dichloromethane and slowly treated with 80 ml of a 4 N dioxane/HCl solution with stirring. The mixture is stirred until the evolution of gas is complete (about 3 h). The product, which is present as a suspension, is finely ground, filtered off with suction, washed with 100 ml of dichlormethane and dried overnight in a high vacuum.

34.5 g (98%) of Example 7 are obtained as a white solid.

MS (CI, NH$_3$, m/e): 442 ([M-glycine+H]$^+$, 100%), 499 ([M+H]$^+$, 20%).

$^1$H-NMR (400 MHz, D$_2$O-d$_2$, δ/ppm): 8.80 (d, J=8.0 Hz; 1H), 8.42 (d, J=8.0 Hz; 1H), 8.35 (d, J=8.0 Hz; 1H), 8.08 (d, J=8.0 Hz; 1H), 7.92 (t, J=8.0 Hz; 1H), 7.82 (dd, J$_1$=7.0 Hz, $J_2$=8.0 Hz; 1H), 7.15 (d, J=10.0 Hz; 2H), 6.98 (d, J=10.0 Hz; 2H), 4.34 (s; 2H), 3.94 (s; 2H), 3.50 (s; 6H), 1.32 (s; 6H).

EXAMPLE 8

4-Acetamidonaphthalene-1-sulphonic Acid N-[4-(N-2,2-Dimethylpropanoyl)aminophenyl]amide

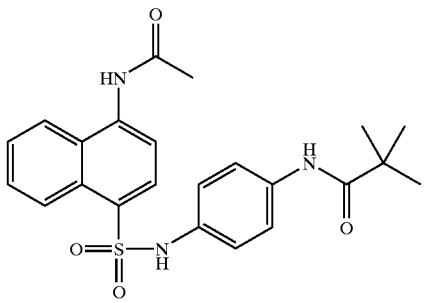

A solution of 3.46 g (18.00 mmol) of 4-(N-2,2-dimethylpropanoyl)aminoaniline (Example IV) in 72 ml of anhydrous pyridine is treated with a solution of 5.87 g (20.70 mmol) of 4-acetamidonaphthalene-1-sulphonyl chloride in 72 ml of anhydrous THF and stirred overnight at 40° C. The solvent mixture is then removed on a rotary evaporator and the residue is stirred with a mixture of 20 ml of ethyl acetate and 150 ml of 2-molar hydrochloric acid. The solid obtained in this process is filtered off with suction and washed with water, a little ethyl acetate and ether.

After drying in a high vacuum, 6.0 g (76%) of Example 8 are obtained in the form of a pale pink-coloured compound which can be crystallized from ethanol.

M.p.:>240 ° C.

$R_f$=0.13 (CH$_2$Cl$_2$/MeOH, 100:5).

MS (CI, NH$_3$, m/e): 457 (M+NH$_4^+$), 440 (M+H$^+$).

$^1$H-NMR (300 MHz, DMSO-d$_6$, δ/ppm): 10.39 (1H, s), 10.11 (1H, s), 8.98 (1H, s), 8.74 (1H, dd), 8.28 (1H, dd), 8.12 (1H, d), 7.91 (1H, d), 7.73 (1H, dt), 7.78 (1H, dt), 7.33 (2H, d), 6.90 (2H, d), 2.21 (3H, s), 1.13 (9H, s).

EXAMPLE 9

4-Aminonaphthalene-1-sulphonic Acid N-[4-(N-2,2-Dimethylpropanoyl)aminophenyl]amide

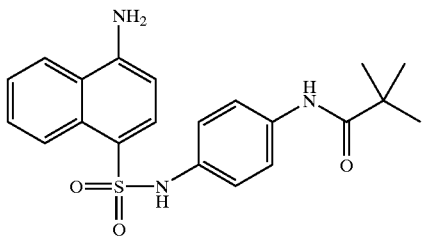

5.83 g (13.26 mmol) of 4-acetamidonaphthalene-1-sulphonic acid N-[4-(N-2,2-dimethylpropanoyl) aminophenyl]amide (Ex. 8) are dissolved in 165 ml of 5% strength aqueous lithium hydroxide solution and warmed to 60° C. for 14 hours. After cooling, the reaction mixture is brought to pH 4 using 2-molar hydrochloric acid. A pale pink-coloured precipitate deposits in this process, which is filtered off with suction and washed with water.

After drying in a high vacuum, 5.0 g (12.58 mmol, 91% yield) are obtained. m.p.: 216 ° C.

$R_f$=0.28 (CH$_2$Cl$_2$/MeOH, 100:5).

MS (CI, NH$_3$, m/e): 415.1 (M+NH$_4^+$), 398 (M+H$^+$).

$^1$H-NMR (300 MHz, DMSO-d$_6$, δ/ppm): 9.98 (1H, s), 8.93 (1H, s), 8.57 (1H, d), 8.17 (1H, d), 7.87 (1H, d), 7.60 (1H, t), 7.45 (1H, t), 7.31 (2H, d), 6.87 (2H, d), 6.69 (2H, s), 6.57 (1H, d), 1.13 (9H, s).

EXAMPLE 10

4-Methylaminonaphthalene-1-sulphonic Acid N-[4-(N-2,2-Dimethylpropanoyl)aminophenyl]amide

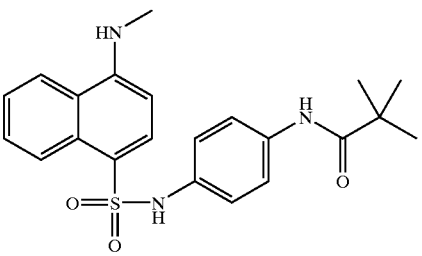

A solution of 1.24 mmol (3.72 mmol) of 3-molar sulphuric acid in 20 ml of THF is treated successively at 0° C. with 1.67 ml (20.6 mmol) of a 37% strength formaldehyde solution, a solution of 1.50 g (3.77 mmol) of 4-aminonaphthalene-1-sulphonic acid N-[4-(N-2,2-dimethylpropanoyl)aminophenyl]amide (Ex. 9) in 20 ml of THF and 1.66 g (26.42 mmol) of solid sodium cyanoborohydride. After two hours at 0° C., the reaction mixture is treated with 30 ml of 2-molar sodium hydroxide solution and concentrated to dryness. The residue is taken up with a mixture of 2-molar hydrochloric acid and a little ethyl acetate. The insoluble residue is filtered off with suction and purified by chromatography (flash chromatography, silica gel, cyclohexane/ethyl acetate, 3:2). Two fractions are obtained. The dimethylamino compound is obtained as a secondary component. The main product is the monomethylamino compound, which is obtained in the form of a white solid.

1.0 g (64%) of Example 10 is obtained.

M.p.: 248° C. (dec.).

$R_f$=0.30 (cyclohexane/ethyl acetate, 3:2).

MS (ESI, m/e): 434 (M+Na$^+$), 412 (M+H$^+$).

$^1$H-NMR (300 MHz, DMSO-d$_6$, δ/ppm): 10.04 (1H, s), 8.94 (1H, s), 8.60 (1H, d), 8.19 (1H, d), 7.97 (1H, d), 7.62 (1H, t), 7.49 (1H, t), 7.32 (2H, d), 7.23 (1H, quart), 6.87 (2H, d), 6.38 (1H, d), 2.88 (3H, d), 1.13 (9H, s).

The compounds shown in Table 1 below are prepared analogously to the abovementioned procedures:

| Ex. No. | Structure |
|---|---|
| 11 | (structure) |
| 12 | (structure) |
| 13 | (structure) |
| 14 | (structure) |
| 15 | (structure) |
| 16 | (structure) |
| 17 | (structure) |

-continued
18
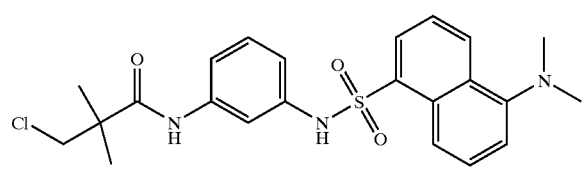
19
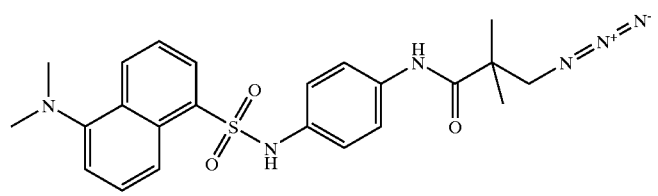
20
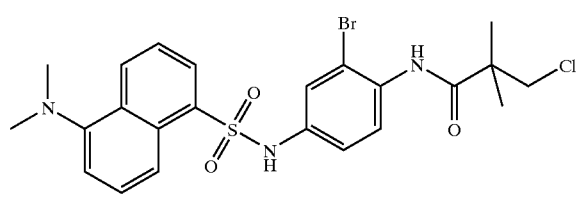
21
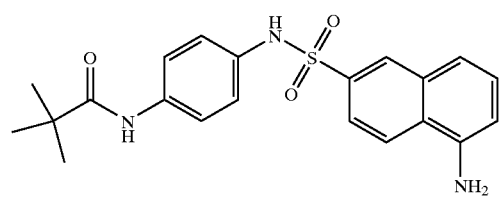
22
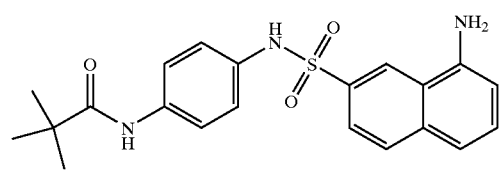
23
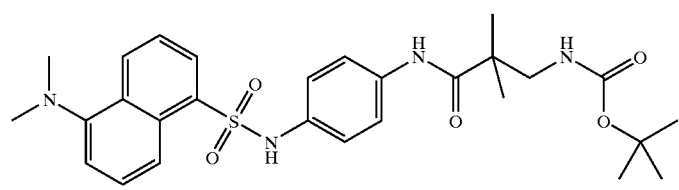
24
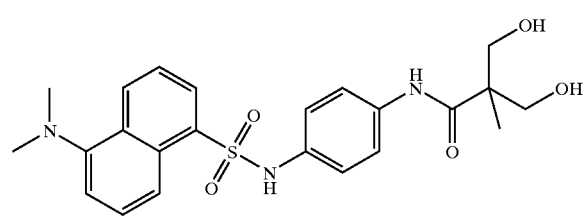
25
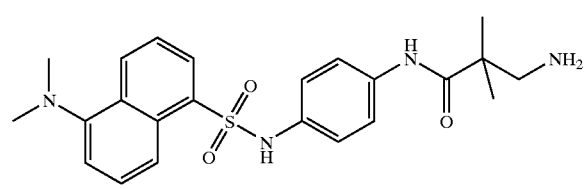

26 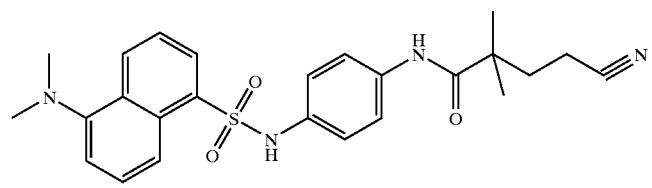
27 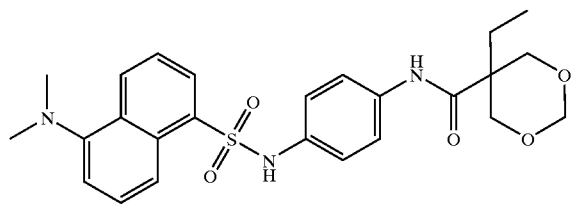
28 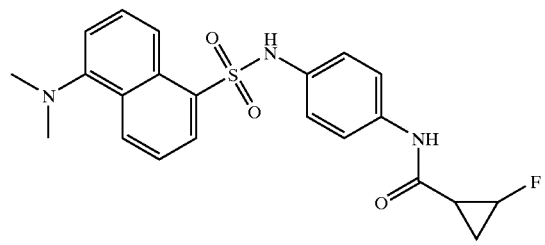
29 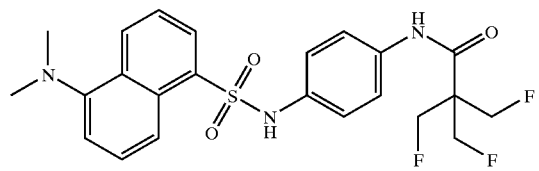
30 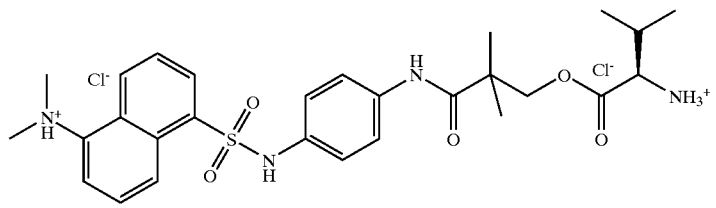
31 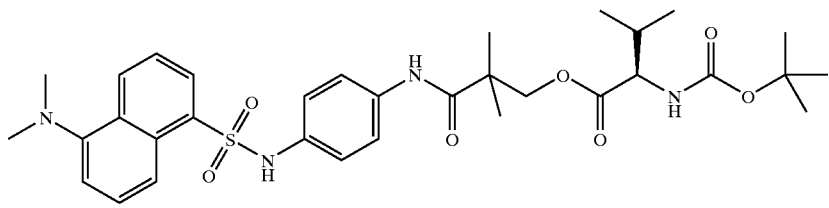
32 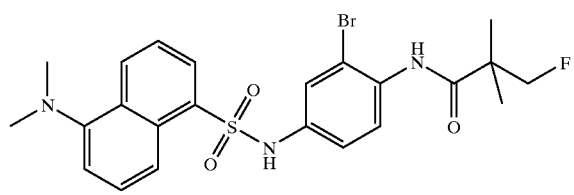

-continued
33
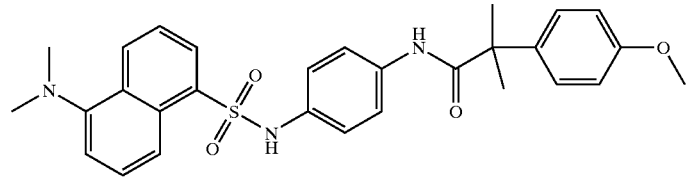
34
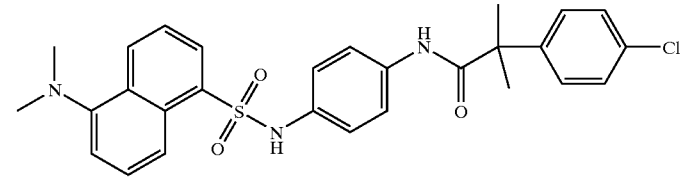
35
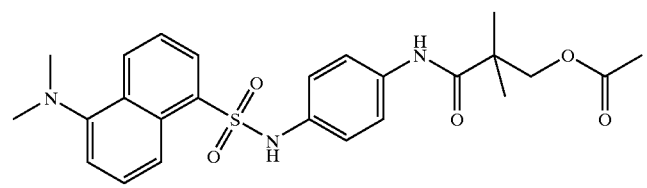
36
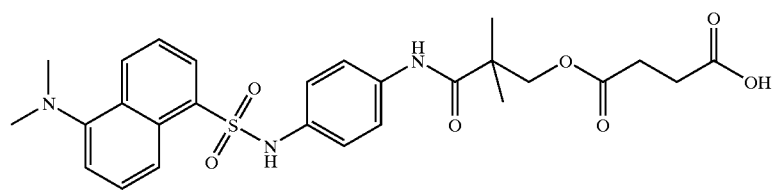
37
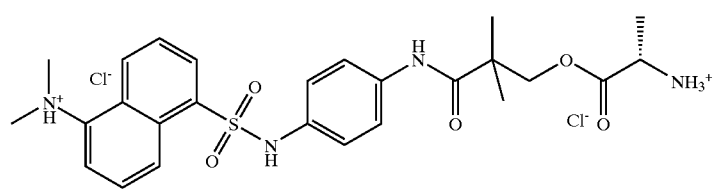
38
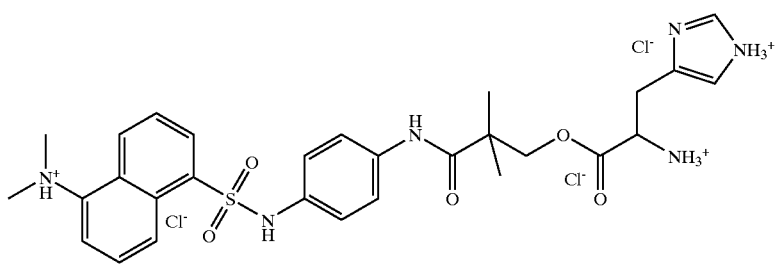
39
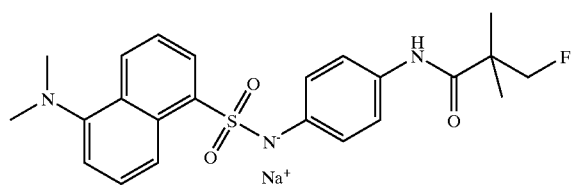

40  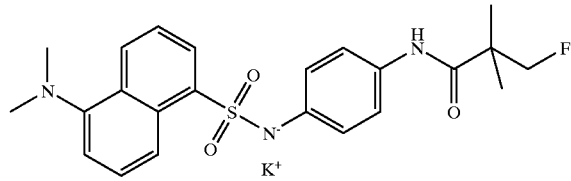
41  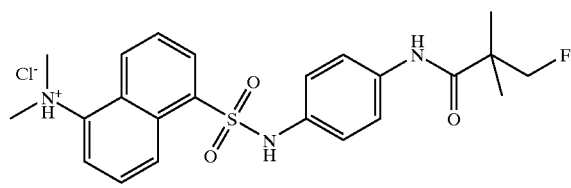
42  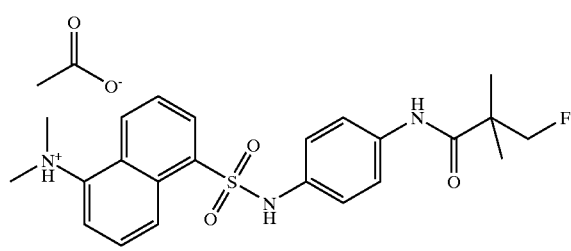
43  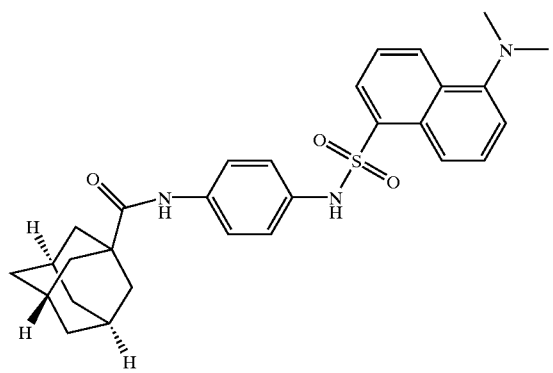
44  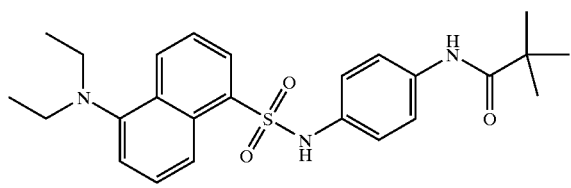
45  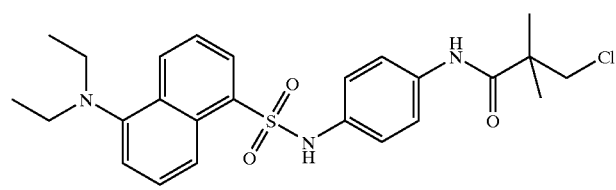
46  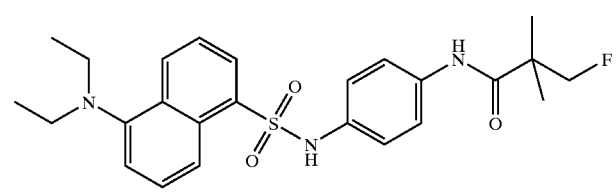

47 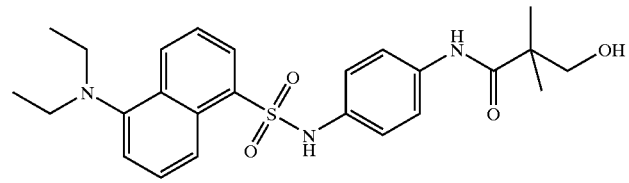
48 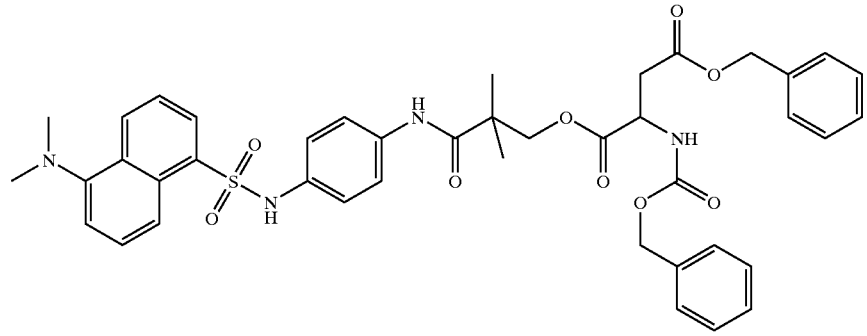
49 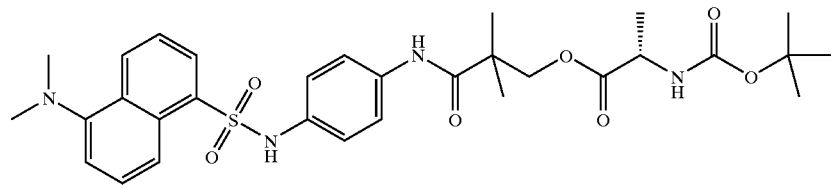
50 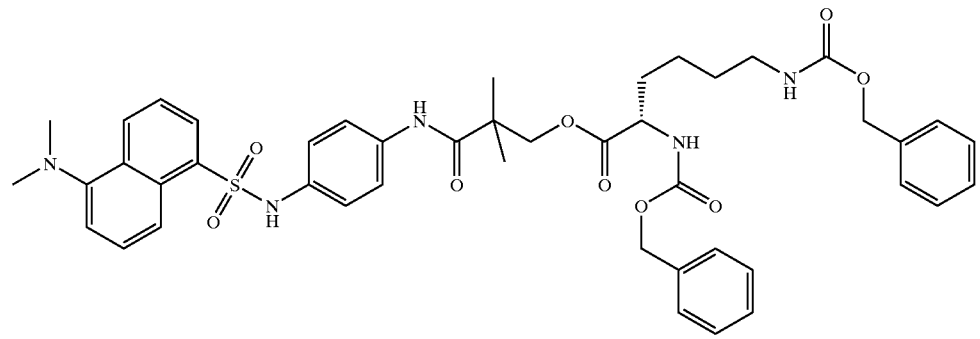
51 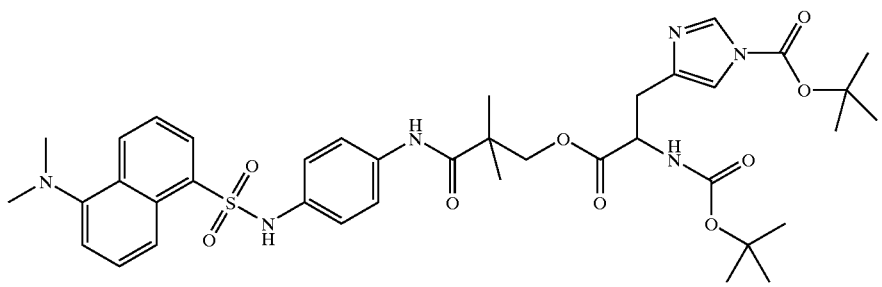
52 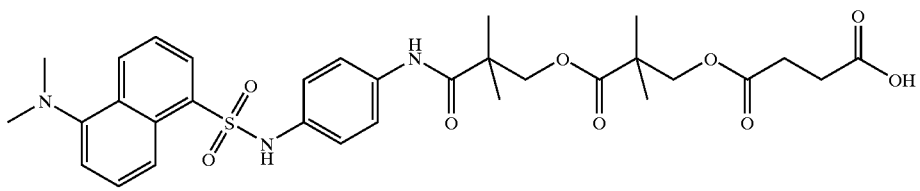

-continued
| | |
|---|---|
| 53 | 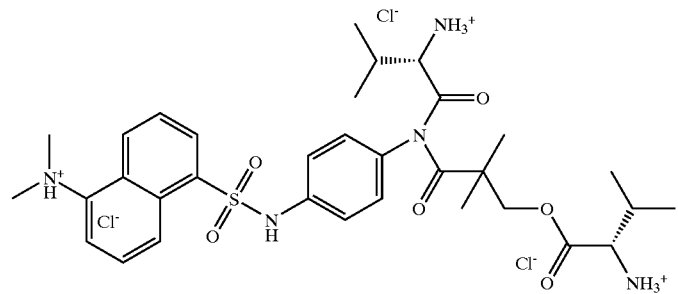 |
| 54 | 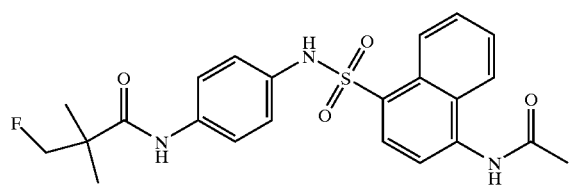 |
| 55 | 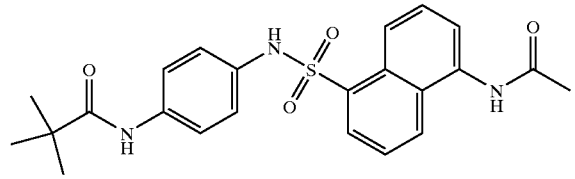 |
| 56 | 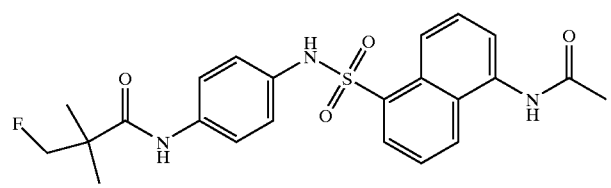 |
| 57 | 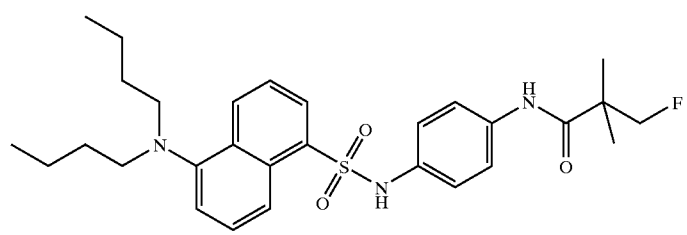 |
| 58 | 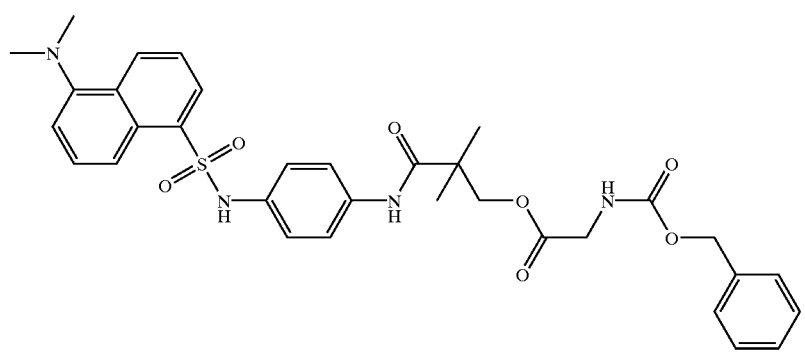 |

59 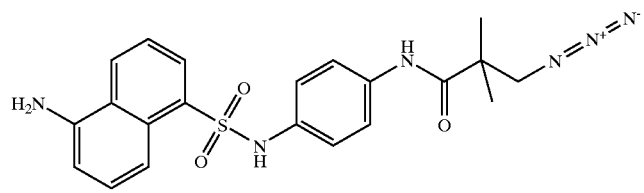
60 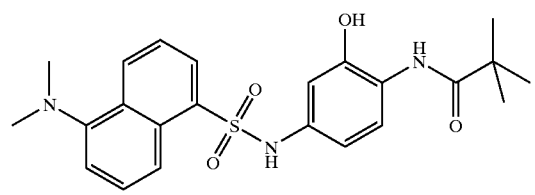
61 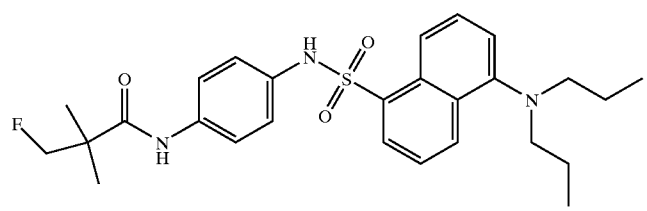
62 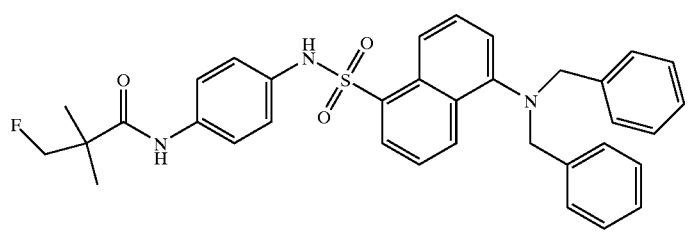
63 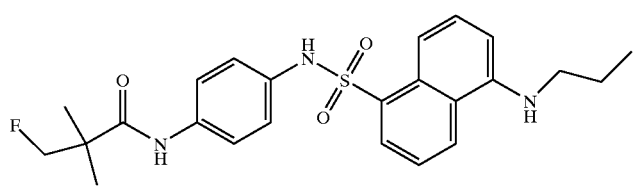
64 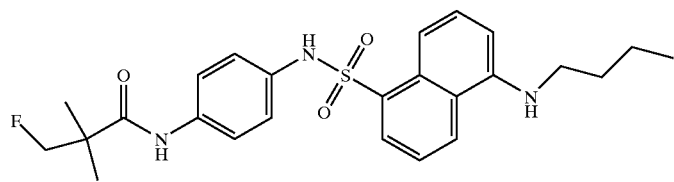
65 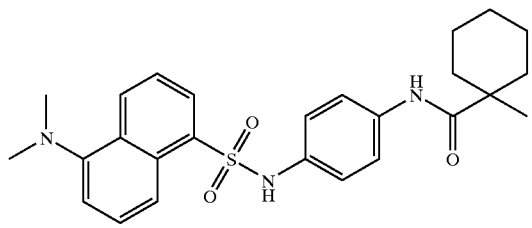

-continued
66 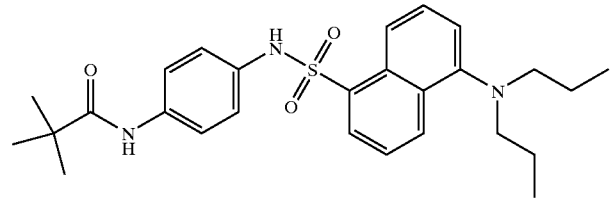
67 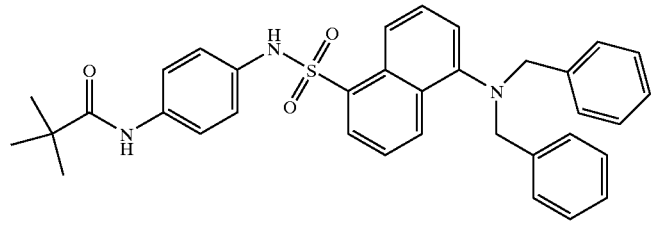
68 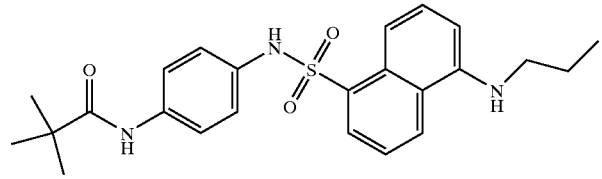
69 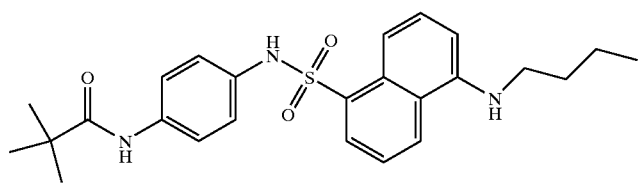
70 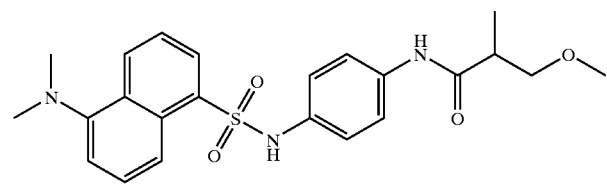
71 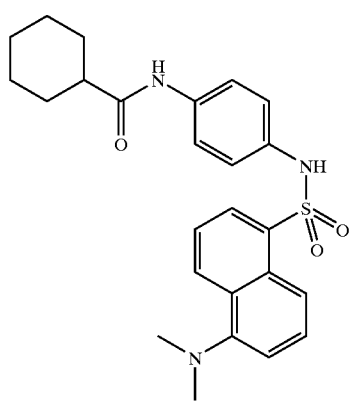

| | |
|---|---|
| 72 | 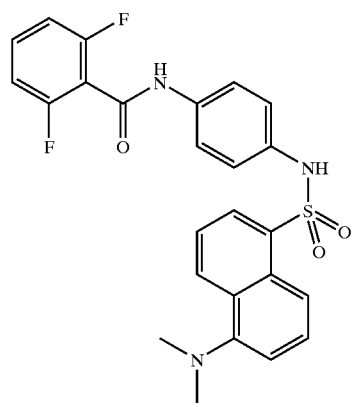 |
| 73 | 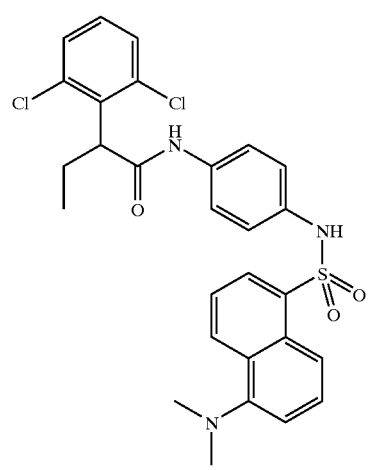 |
| 74 | 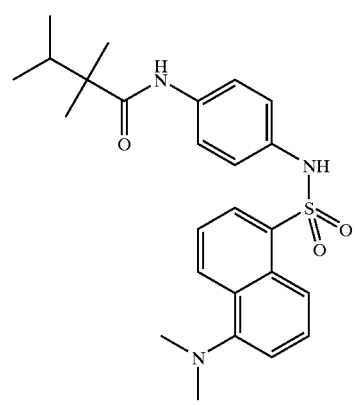 |

-continued
75
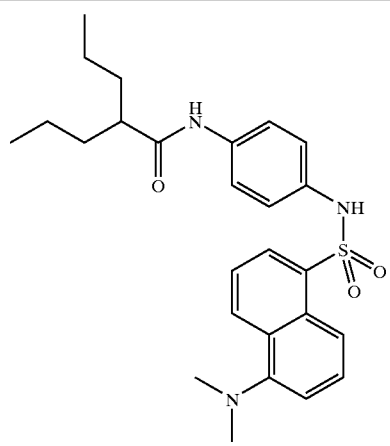
76
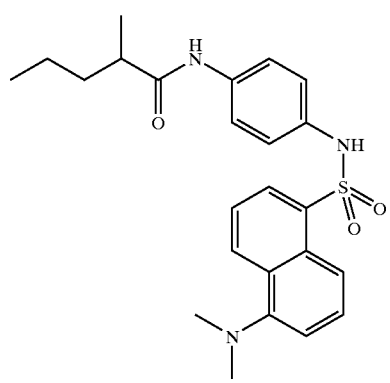
77
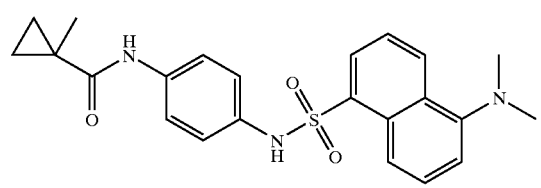
78
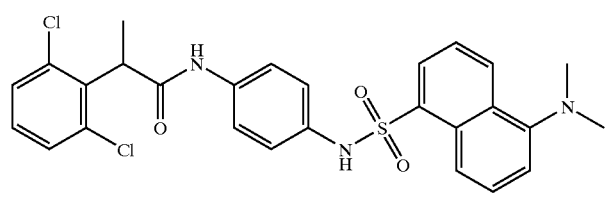
79
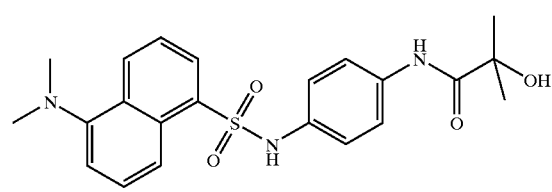
80
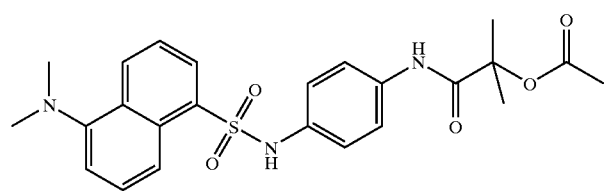

-continued
81 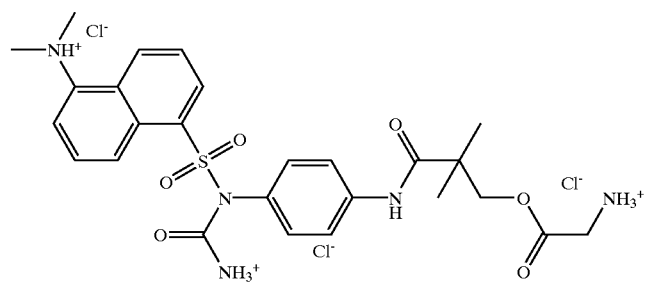
82 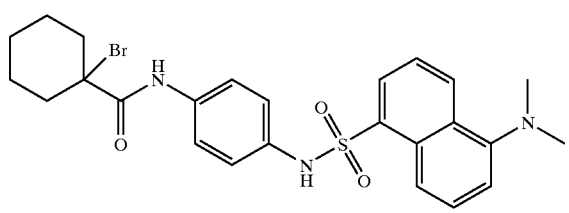
83 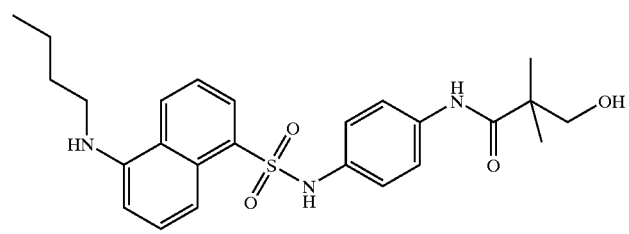
84 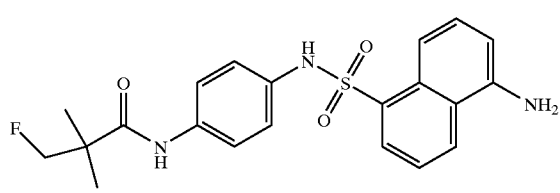
85 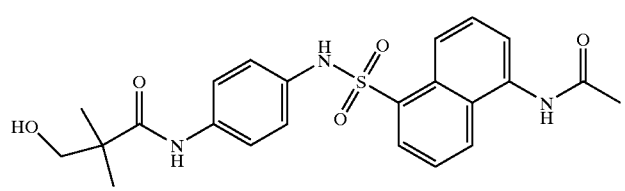
86 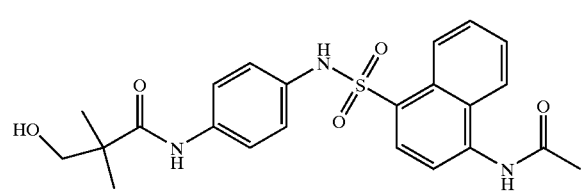
87 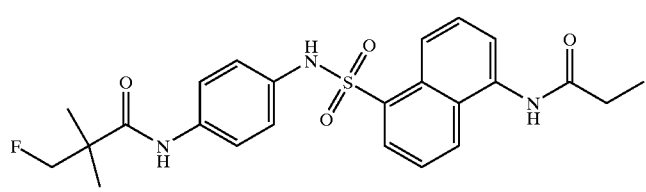

| | |
|---|---|
| 88 | 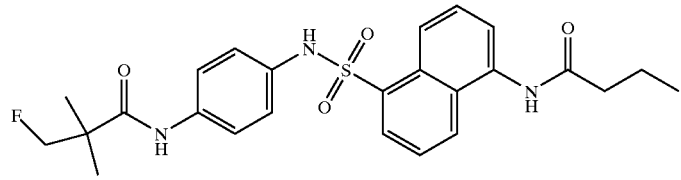 |
| 89 | 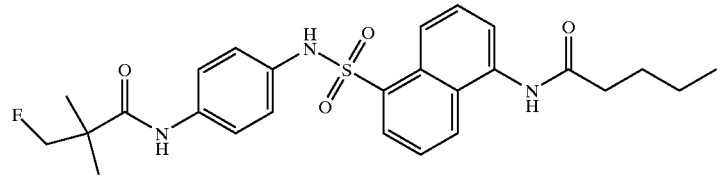 |
| 90 | 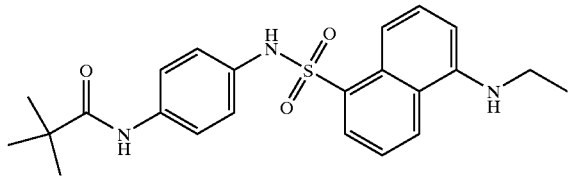 |
| 91 | 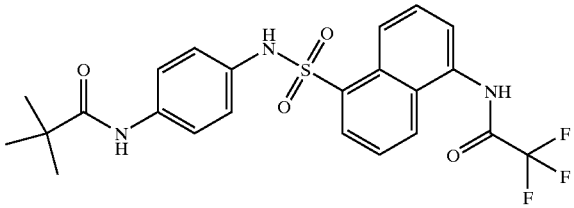 |
| 92 | 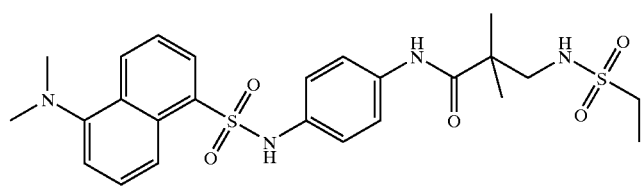 |
| 93 | 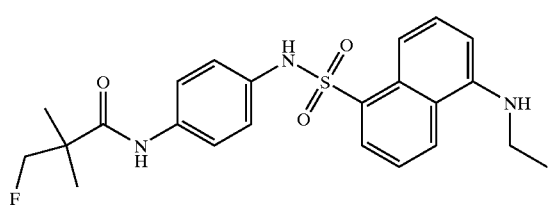 |
| 94 | 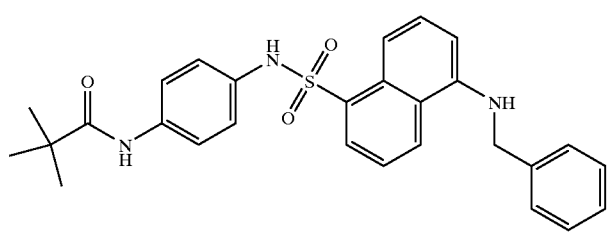 |

95 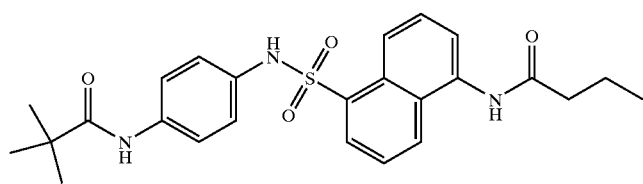
96 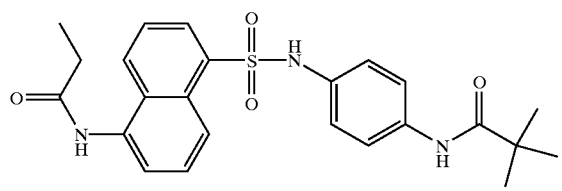
97 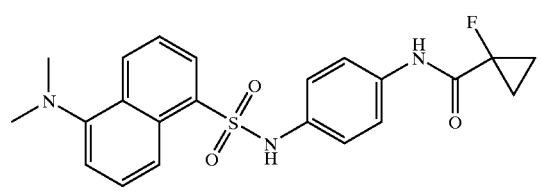
98 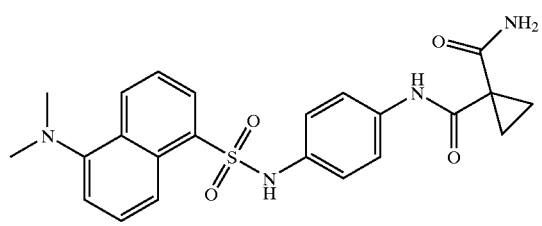
99 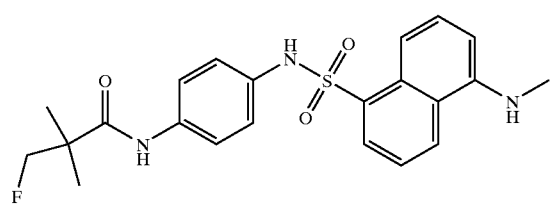
100 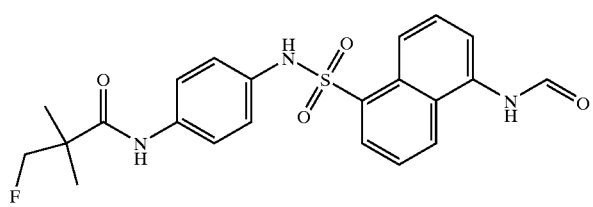
101 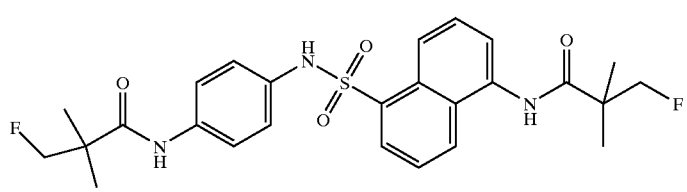
102 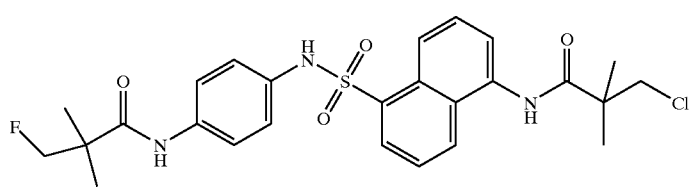

-continued
103 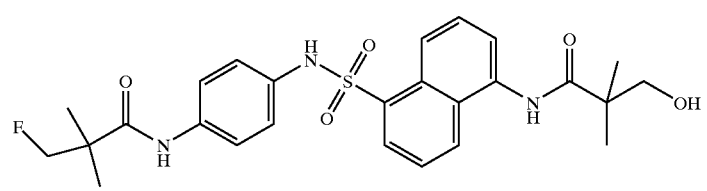
104 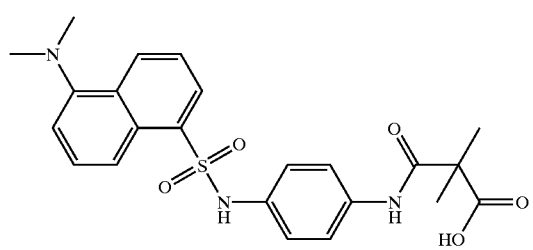
105 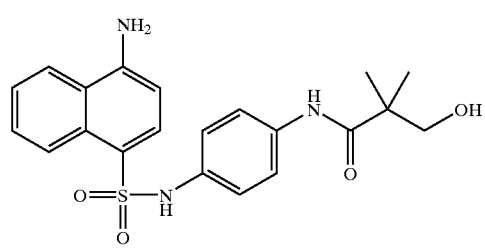
106 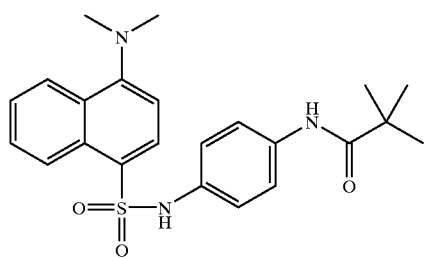
107 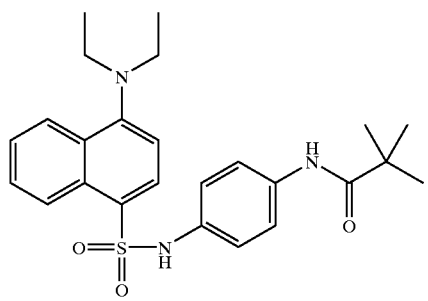
108 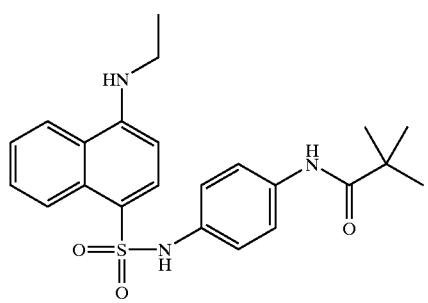

-continued
| 109 | 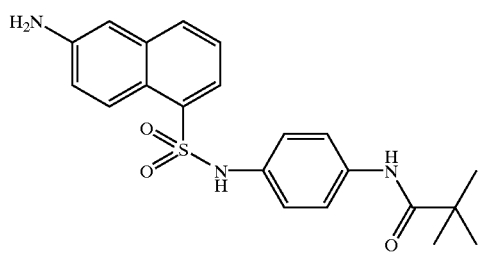 |
| 110 | 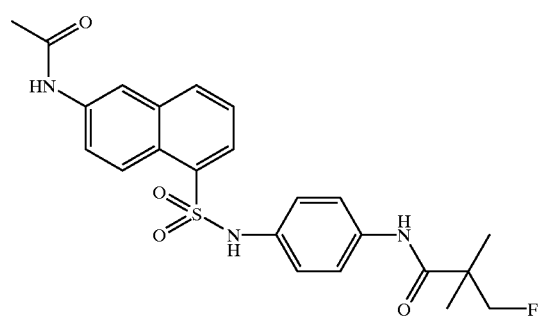 |
| 111 | 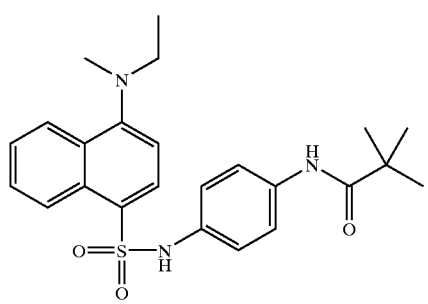 |
| 112 | 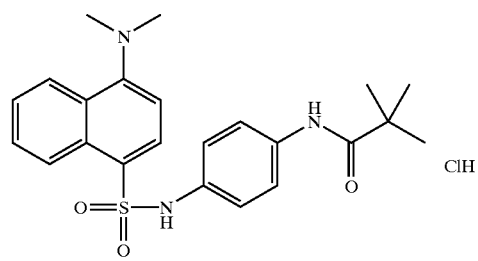 |
| 113 | 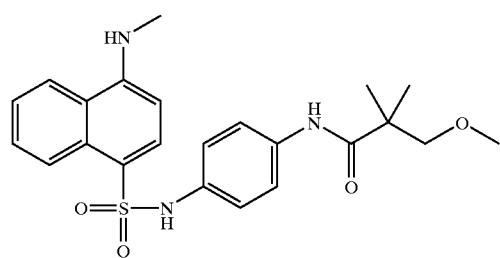 |

114 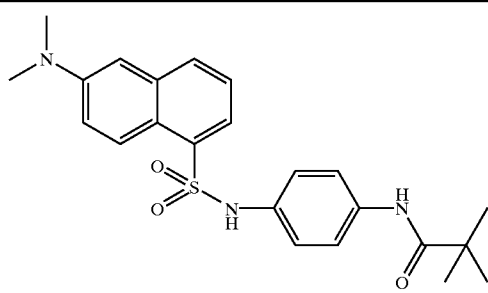
115 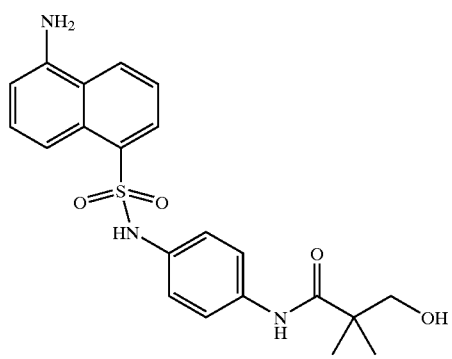
116 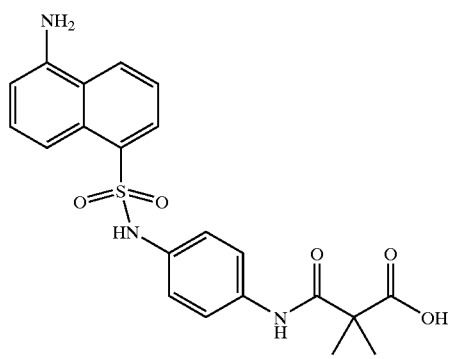
117 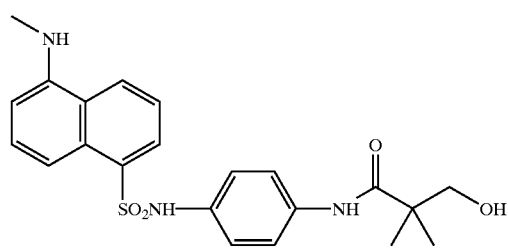
| Ex. No. | Mw | $R_f$ | M.p. [° C.] |
| --- | --- | --- | --- |
| 11 | 509,7165 | 0.83 (Q) | |
| 12 | 439,5811 | | 160 |
| 13 | 443,5444 | | 161 |
| 14 | 461,5348 | 0.57 (Q) | |
| 15 | 439,5374 | 0.29 (U) | |
| 16 | 459,999 | | 187 |
| 17 | 425,554 | | 108 |
| 18 | 459,999 | | 105 |
| 19 | 466,5661 | | 153 |
| 20 | 538,895 | 0.7 (Q) | |
| 21 | 397,4998 | 0.23 (Q) | |
| 22 | 397,4998 | 0.35 (Q) | |
| 23 | 540,687 | 0.45 (Q) | |
| 24 | 457,5528 | 0.15 (Q) | |
| 25 | 440,5686 | 0.14 (U) | |

-continued

| | | | |
|---|---|---|---|
| 26 | 464,5909 | | 174 |
| 27 | 483,591 | 0.13 (Q) | |
| 28 | 427,5014 | 0.19 (Q) | |
| 29 | 479,5253 | 0.73 (Q) | |
| 30 | 613,6089 | | 150 dec. |
| 31 | 640,8052 | 0.63 (Q) | |
| 32 | 522,4404 | 0.7 (Q) | |
| 33 | 517,6522 | 0.58 (Q) | |
| 34 | 522,0707 | 0.67 (Q) | |
| 35 | 483,591 | 0.35 (Q) | |
| 36 | 541,6281 | 0.35 (U) | |
| 37 | 585,5547 | | 120–130 dec. |
| 38 | 688,0785 | | 120–130 dec. |
| 39 | 465,5262 | | 110 dec. |
| 40 | 481,6384 | | 110 dec. |
| 41 | 480,0054 | | 125 dec. |
| 42 | 503,5974 | | 145 |
| 43 | 503,6687 | 0.82 (Z) | |
| 44 | 453,6081 | 0.7 (Z) | |
| 45 | 488,0532 | 0.7 (Z) | |
| 46 | 471,5986 | 0.7 (Z) | |
| 47 | 469,6075 | 0.25 (Z) | |
| 48 | 780,9045 | 0.29 (Z) | |
| 49 | 612,7511 | 0.4 (Z) | |
| 50 | 838,0004 | 0.18 (Z) | |
| 51 | 778,9323 | 0.13 (Z) | |
| 52 | 641,7464 | 0.45 (U) | |
| 53 | 749,2034 | | 150–160 dec. |
| 54 | 457,5279 | 0.06 (Z) | |
| 55 | 439,5374 | 0.2 (ZB) | |
| 56 | 457,5279 | 0.19 (ZB) | |
| 57 | 527,7069 | 0.85 (Z) | |
| 58 | 632,7415 | | 152 |
| 59 | 438,5119 | 0.2 (Z) | |
| 60 | 441,5533 | 0.5 (Z) | |
| 61 | 499,6528 | 0.76 (Z) | |
| 62 | 595,742 | 0.7 (Z) | |
| 63 | 457,5715 | 0.57 (Z) | |
| 64 | 471,5986 | 0.63 (Z) | |
| 65 | 465,6193 | 0.68 (Z) | |
| 66 | 481,6623 | 0.77 (Z) | |
| 67 | 577,7516 | 0.65 (Z) | |
| 68 | 439,5811 | 0.6 (Z) | |
| 69 | 453,6081 | 0.67 (Z) | |
| 70 | 441,5533 | 0.22 (Z) | |
| 71 | 451,5922 | | 219 |
| 72 | 481,5252 | | 191 |
| 73 | 556,5157 | | 169 |
| 74 | 453,6081 | 0.52 (Q) | |
| 75 | 467,6352 | 0.54 (Q) | |
| 76 | 439,5811 | 0.51 (Q) | |
| 77 | 423,538 | 0.5 (Z) | |
| 78 | 542,4886 | 0.63 (Z) | |
| 79 | 427,5262 | 0.54 (U) | |
| 80 | 469,5639 | 0.31 (Z) | |
| 81 | 665,041 | | 210 |
| 82 | 530,4882 | 0.65 (Z) | |
| 83 | 469,6075 | 0.24 (Z) | |
| 84 | 415,4902 | 0.19 (Z) | |
| 85 | 455,5368 | 0.25 (U) | |
| 86 | 455,5368 | 0.26 (U) | |
| 87 | 471,5549 | 0.23 (ZA) | |
| 88 | 485,582 | 0.31 (ZA) | |
| 89 | 499,6091 | 0.42 (ZA) | |
| 90 | 425,554 | 0.55 (Z) | |
| 91 | 493,5087 | 0.53 (Z) | |
| 92 | 532,6856 | 0.53 (U) | |
| 93 | 443,5444 | 0.52 (Z) | |
| 94 | 487,6257 | 0.62 (Z) | |
| 95 | 467,5916 | 0.48 (Z) | |
| 96 | 453,5645 | 0.11 (Z) | |
| 97 | 427,5014 | 0.69 (Z) | |
| 98 | 452,5361 | 0.15 (ZA) | |
| 99 | 429,5173 | 0.58 (Z) | |
| 100 | 443,5008 | 0.12 (Z) | |
| 101 | 517,5995 | 0.21 (Z) | |
| 102 | 534,0541 | 0.21 (Z) | |
| 103 | 515,6085 | 0.10 (Z) | |
| 104 | 455,5368 | | 98 |

-continued

| | | |
|---|---|---|
| 105 | 413,4992 | 163 dec. |
| 106 | 425,554 | 204 dec. |
| 107 | 453,6081 | 181 |
| 108 | 425,554 | 265 |
| 109 | 397,4998 | 129 |
| 110 | 457,5279 | 163 |
| 111 | 439,5811 | 166 |
| 112 | 462,015 | 174 dec. |
| 113 | 441,5533 | 0.23 (E) |
| 114 | 425,554 | 249 |
| 115 | 413,4992 | 225–230 |
| 116 | 427,4826 | 115 |
| 117 | 427,526 | 163 |

What is claimed is:

1. Sulphonamides of the general formula (I)

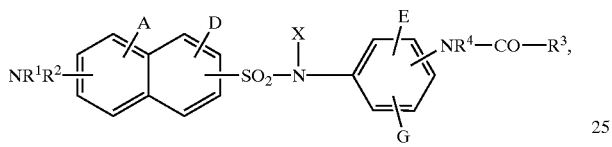

in which
- $R^1$ and $R^2$ are identical or different and represent hydrogen, formyl, phenyl or benzyl optionally substituted by one to three halogen atoms, or straight-chain or branched alkyl or acyl each having up to 6 carbon atoms, where alkyl or acyl can optionally be substituted by one to three substituents selected from halogen and hydroxyl,
- A, D, E and G are identical or different and represent hydrogen, halogen, nitro, cyano, hydroxyl, carboxyl, trifluoromethyl, trifluoromethoxy or straight-chain or branched alkyl, alkoxy or alkoxycarbonyl each having up to 5 carbon atoms,
- $R^3$ represents straight-chain or branched alkenyl having up to 6 carbon atoms, or represents straight-chain or branched alkyl having up to 8 carbon atoms, which optionally carries an amino group which can optionally be substituted by alkyl having up to 4 carbon atoms or by an amino protective group, or the alkyl is optionally identically or differently substituted one to 3 times by hydroxyl, cyano, halogen, azido, nitro, trifluoromethyl, carboxyl or phenyl which, for its part, can be identically or differently substituted up to 2 times by nitro, halogen, hydroxyl or by straight-chain or branched alkyl or alkoxy having up to 4 carbon atoms, or
- $R^3$ represents radicals of the formula

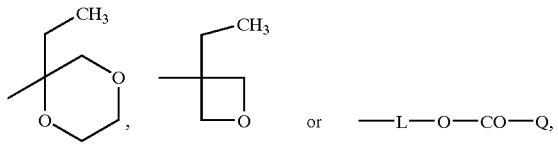

in which
- L represents a straight-chain or branched alkanediyl group having up to 6 carbon atoms,
- Q represents alkyl having up to 6 carbon atoms, which is optionally substituted by carboxyl, or represents radicals of the formula

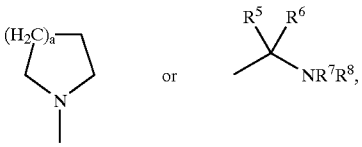

in which
- a denotes the number 1 or 2,
- $R^5$ denotes hydrogen,
- $R^6$ denotes cycloalkyl having 3 to 8 carbon atoms or aryl having 6 to 10 carbon atoms or hydrogen, or denotes straight-chain or branched alkyl having up to 8 carbon atoms,
- where the alkyl is optionally substituted by cyano, methylthio, hydroxyl, mercapto, guanidyl or by a group of the formula —$NR^9R^{10}$ or $R^{11}$—OC—,
  in which
  - $R^9$ and $R^{10}$ independently of one another denote hydrogen, straight-chain or branched alkyl having up to 8 carbon atoms or phenyl, and
  - $R^{11}$ denotes hydroxyl, benzyloxy, alkoxy having up to 6 carbon atoms or the abovementioned group —$NR^9R^{10}$,
- or the alkyl is optionally substituted by cycloalkyl having 3 to 8 carbon atoms or by aryl having 6 to 10 carbon atoms which, for its part, is substituted by hydroxyl, halogen, nitro, alkoxy having up to 8 carbon atoms or by the group —$NR^9R^{10}$,
  in which
  - $R^9$ and $R^{10}$ have the meaning indicated above,
- or the alkyl is optionally substituted by a 5- to 6-membered nitrogen-containing heterocycle or by indolyl, in which the corresponding —NH functions are optionally substituted by alkyl having up to 6 carbon atoms or protected by an amino protective group,
- $R^7$ and $R^8$ are identical or different and denote hydrogen or an amino protective group,
- $R^4$ denotes hydrogen or a radical of the formula

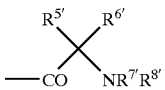

in which
- $R^{5'}$, $R^{6'}$, $R^{7'}$ and $R^{8'}$ have the meaning of $R^5$, $R^6$, $R^7$ and $R^8$ indicated above and are identical to or different from this, X has the meaning of $R^4$ indicated above and can be identical to or different from this meaning,
and their stereoisomers, stereoisomeric mixtures and salts, with the exception of N-[4-[[[5-(dimethylamino)-1-naphthalenyl]sulphonyl]amino]phenyl]acetamide.

2. Sulphonamides of the general formula (I) according to claim 1, in which $R^1$ and $R^2$ are identical or different and represent hydrogen, phenyl or straight-chain or branched alkyl or acyl each having up to 6 carbon atoms, A, D, E and G are identical or different and represent hydrogen, halogen, nitro, cyano, hydroxyl, carboxyl, trifluoromethyl, trifluoromethoxy or straight-chain or branched alkyl, alkoxy or alkoxycarbonyl each having up to 5 carbon atoms, $R^3$ represents straight-chain or branched alkenyl having up to 6 carbon atoms, or represents straight-chain or branched alkyl having up to 8 carbon atoms, which optionally carries an amino group which can be substituted by alkyl having up to 4 carbon atoms or by an amino protective group, or the alkyl is optionally identically or differently substituted one to 3 times by hydroxyl, cyano, halogen, azido, nitro, trifluoromethyl, carboxyl or phenyl which, for its part, can be identically or differently substituted up to 2 times by nitro, halogen, hydroxyl or by straight-chain or branched alkyl or alkoxy having up to 4 carbon atoms, or $R^3$ represents radicals of the formula

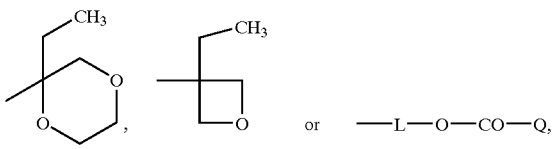

in which

L represents a straight-chain or branched alkanediyl group having up to 6 carbon atoms, Q represents alkyl having up to 6 carbon atoms, which is optionally substituted by carboxyl, or represents radicals of the formula

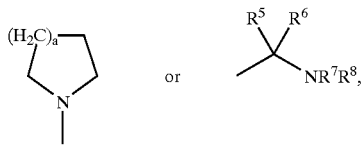

in which a denotes the number 1 or 2, $R^5$ denotes hydrogen, $R^6$ denotes cycloalkyl having 3 to 8 carbon atoms or aryl having 6 to 10 carbon atoms or hydrogen, or denotes straight-chain or branched alkyl having up to 8 carbon atoms, where the alkyl is optionally substituted by cyano, methylthio, hydroxyl, mercapto, guanidyl or by a group of the formula $-NR^9R^{10}$ or $R^{10}-OC-$, in which $R^9$ and $R^{10}$ independently of one another denote hydrogen, straight-chain or branched alkyl having up to 8 carbon atoms or phenyl, and $R^{11}$ denotes hydroxyl, benzyloxy, alkoxy having up to 6 carbon atoms or the abovementioned group $-NR^9R^{10}$, or the alkyl is optionally substituted by cycloalkyl having 3 to 8 carbon atoms or by aryl having 6 to 10 carbon atoms which, for its part, is substituted by hydroxyl, halogen, nitro, alkoxy having up to 8 carbon atoms or by the group $-NR^9R^{10}$, in which $R^9$ and $R^{10}$ have the meaning indicated above, or the alkyl is optionally substituted by a 5- to 6-membered nitrogen-containing heterocycle or by indolyl, in which the corresponding $-NH$ functions are optionally substituted by alkyl having up to 6 carbon atoms or protected by an amino protective group, $R^7$ and $R^8$ are identical or different and denote hydrogen or an amino protective group, $R^4$ represents hydrogen or a radical of the formula

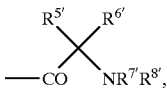

in which $R^{5'}$, $R^{6'}$, $R^{7'}$ and $R^{8'}$ have the meaning of $R^5$, $R^6$, $R^7$ and $R^8$ indicated above and are identical to or different from these, and X represents hydrogen, and their stereoisomers, stereoisomer mixtures and salts, with the exception of N-[4-[[[5-(dimethylamino)-1-naphthalenyl]sulphonyl]amino]phenyl]acetamide.

3. Sulphonamides of the general formula (I) according to claim 1 or 2, in which $R^3$ represents straight-chain or branched alkenyl having up to 6 carbon atoms, or represents straight-chain or branched alkyl having up to 8 carbon atoms, in which the alkyl carries an amino group which can be substituted by alkyl having up to 4 carbon atoms or by an amino protective group, or the alkyl is identically or differently substituted one to 3 times by hydroxyl, cyano, halogen, azido, nitro, trifluoromethyl, carboxyl or phenyl which, for its part, can be identically or differently substituted up to 2 times by nitro, halogen or hydroxyl or by straight-chain or branched alkyl or alkoxy having up to 4 carbon atoms, or $R^3$ represent radicals of the formula

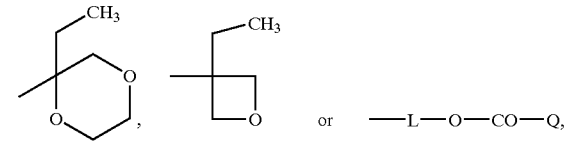

in which L and Q are as defined above.

4. Sulphonamides of the general formula (I) according to claim 1 or 2, in which $R^1$ and $R^2$ are identical or different and represent hydrogen, phenyl or straight-chain or branched alkyl or acyl each having up to 5 carbon atoms, A, D, E and G are identical or different and represent hydrogen, fluorine, chlorine, bromine, nitro, cyano, hydroxyl or straight-chain or branched alkyl, alkoxy or alkoxycarbonyl each having up to 3 carbon atoms, $R^3$ represents straight-chain or branched alkenyl having up to 5 carbon atoms, or represents straight-chain or branched alkyl having up to 7 carbon atoms which optionally carries an amino group which can be substituted by alkyl having up to 3 carbon atoms, tert-butyloxycarbonyl or benzyloxycarbonyl, or the alkyl is optionally identically or differently substituted one to 3 times by hydroxyl, cyano, fluorine, chlorine, azido, nitro, trifluoromethyl or phenyl which, for its part, can be identically or differently substituted up to 2 times by nitro, fluorine, chlorine or hydroxyl or by straight-chain or branched alkyl or alkoxy having up to 3 carbon atoms, or $R^3$ represent radicals of the formula

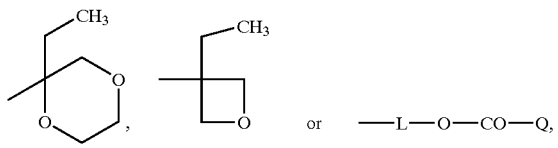

in which
L represents a straight-chain or branched alkanediyl group having up to 4 carbon atoms,
Q represents alkyl having up to 4 carbon atoms, which is optionally substituted by carboxyl, or represents radicals of the formula

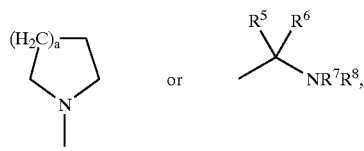

in which
a denotes the number 1 or 2,
$R^5$ denotes hydrogen,
$R^6$ denotes cyclopentyl, cyclohexyl, phenyl or hydrogen, or denotes straight-chain or branched alkyl having up to 6 carbon atoms,
where the alkyl can optionally be substituted by cyano, methylthio, hydroxyl, mercapto, guanidyl, amino, carboxyl or $H_2N-CO-$,
or the alkyl is substituted by cyclohexyl, naphthyl or phenyl which, for its part, can be substituted by fluorine, hydroxyl, nitro or alkoxy having up to 4 carbon atoms,
or the alkyl is substituted by indolyl, imidazolyl, pyridyl, triazolyl or pyrazolyl, where the corresponding —NH functions are optionally substituted by alkyl having up to 4 carbon atoms or protected by tert-butyloxycarbonyl or benzyloxycarbonyl,
$R^7$ and $R^8$ are identical or different and denote hydrogen, tert-butyloxycarbonyl or benzyloxycarbonyl,
$R^4$ represents hydrogen or a radical of the formula

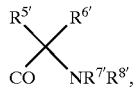

in which
$R^{5'}$, $R^{6'}$, $R^{7'}$ and $R^{8'}$ have the meaning of $R^5$, $R^6$, $R^7$ and $R^8$ indicated above and are identical to or different from these, and their stereoisomers, stereoisomer mixtures and salts, with the exception of N-[4-[[[5-(dimethylamino)-1-naphthalenyl]sulphonyl]amino]phenyl]acetamide.

5. Sulphonamides of the general formula (I) according to claim 4, in which
$R^3$ represents straight-chain or branched alkenyl having up to 5 carbon atoms, or
$R^3$ represents straight-chain or branched alkyl having up to 7 carbon atoms, in which the alkyl carries an amino group which can be substituted by alkyl having up to 3 carbon atoms, tert-butyloxycarbonyl or benzyloxycarbonyl, or the alkyl is identically or differently substituted one to 3 times by hydroxyl, cyano, fluorine, chlorine, azido, nitro, trifluoromethyl or phenyl which, for its part, can be identically or differently substituted up to 2 times by nitro, fluorine, chlorine or hydroxyl or by straight-chain or branched alkyl or alkoxy having up to 3 carbon atoms, or
$R^3$ represents radicals of the formula

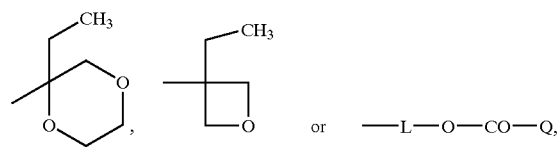

in which L and Q are as defined above.
6. Sulphonamides of the general formula (I) according to claim 1, in which
$R^1$ and $R^2$ are identical or different and represent hydrogen, phenyl or straight-chain or branched alkyl or acyl each having up to 4 carbon atoms,
A, D, E and G are identical or different and represent hydrogen, fluorine, chlorine, bromine, hydroxyl, methyl or methoxy,
$R^3$ represents straight-chain or branched alkyl having up to 4 carbon atoms, or represents straight-chain or branched alkyl having up to 5 carbon atoms, which optionally carries an amino group which can be substituted by tert-butyloxycarbonyl or benzyloxycarbonyl, or which is optionally identically or differently substituted one to 3 times by hydroxyl, cyano, fluorine, chlorine, nitro, azido, trifluoromethyl or phenyl which, for its part, can be identically or differently substituted up to 2 times by nitro, fluorine, chlorine, hydroxyl, methyl, ethyl, methoxy or ethoxy, or
$R^3$ represents radicals of the formula

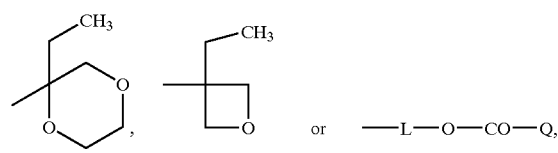

in which
L represents a straight-chain or branched alkanediyl group having up to 4 carbon atoms,
Q represents alkyl having up to 3 carbon atoms, which is optionally substituted by carboxyl, or represents a radical of the formula

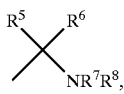

in which
R⁵ denotes hydrogen,
R⁶ denotes cyclopentyl, cyclohexyl or hydrogen, or denotes straight-chain or branched alkyl having up to 4 carbon atoms,
where the alkyl can optionally be substituted by cyano, methylthio, hydroxyl, mercapto, guanidyl, amino, carboxyl or H₂N—CO—,
or the alkyl is substituted by cyclohexyl, naphthyl or phenyl which, for its part, can be substituted by fluorine, chlorine or alkoxy having up to 4 carbon atoms,
or the alkyl is substituted by indolyl, imidazolyl, triazolyl, pyridyl or pyrazolyl, where the corresponding —NH functions are optionally substituted by methyl or protected by benzyloxymethylene or tert-butyloxycarbonyl (BOC),
R⁷ and R⁸ are identical or different and denote hydrogen or tert-butyloxycarbonyl,
R⁴ represents hydrogen or a radical of the formula

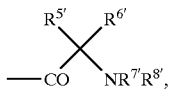

in which
R⁵', R⁶', R⁷' and R⁸' have the meaning of R⁵, R⁶, R⁷ and R⁸ indicated above and are identical to or different from these,
and their stereoisomers, stereoisomer mixtures and salts, with the exception of N-[4-[[[5-(dimethylamino)-1-naphthalenyl]sulfonyl]-amino]phenyl]acetamide.

7. Sulfonamides of the general formula (I) according to claim 1 in which
R³ represents straight-chain or branched alkenyl having up to 4 carbon atoms, or represents straight-chain or branched alkyl having up to 5 carbon atoms, in which the alkyl carries an amino group which can be substituted by tert-butyloxycarbonyl or benzyloxycarbonyl, or the alkyl is identically or differently substituted one to 3 times by hydroxyl, cyano, fluorine, chlorine, nitro, azido, trifluoromethyl or phenyl which, for its part, can be identically or differently substituted up to 2 times by nitro, fluorine, chlorine, hydroxyl, methyl, ethyl, methoxy or ethoxy, or
R³ represents radicals of the formula

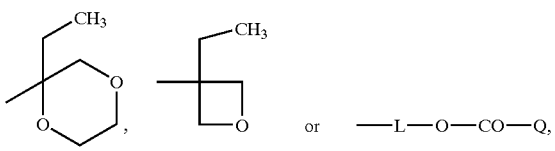

in which L or Q are as defined above, and their stereoisomers, stereoisomeric mixtures and salts.

8. Sulphonamides of the general formula (I) according to claim 1 in which
R¹ and R² represent straight-chain or branched alkyl having up to 4 carbon atoms, A, D, E and G represent hydrogen,
R³ represents straight-chain or branched alkyl having up to 5 carbon atoms, which is substituted by hydroxyl, or
R³ represents a radical of the formula

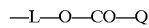

in which
L represents a straight-chain or branched alkanediyl group having up to 4 carbon atoms,
Q represents a radical of the formula

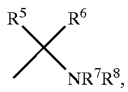

in which
R⁵ and R⁶ denote hydrogen, and
R⁷ and R⁸ denote hydrogen, and
R⁴ represents hydrogen and their stereoisomers, stereoisomeric mixtures and salts.

9. Sulphonamides of the general formula (I) according to claim 1 which are selected from the group of the following compounds:

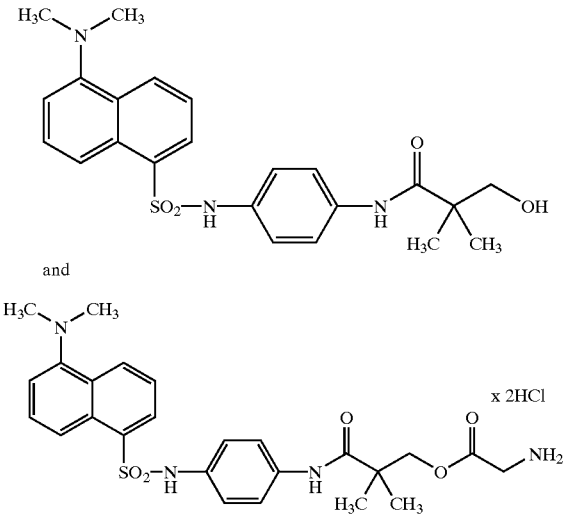

10. A pharmaceutical composition comprising a sulphonamide of the general formula (I) according to claim 1 and a pharmaceutically-acceptable carrier.

11. A method of treating a viral disorder involving a virus of the herpesviridae group, comprising administering to a patient in need thereof an effective amount of a sulphonamide of the general formula (I) according to claim 1.

12. The method of claim 11, wherein said virus of the herpesviridae group is cytomegalovirus.

13. Process for the preparation of compounds of the general formula (I), characterized in that (A) compounds of the general formula (II)

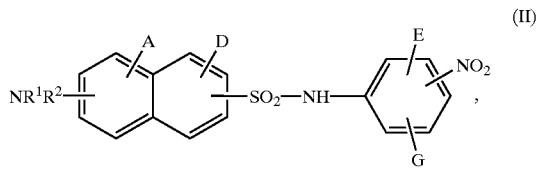

in which
A, D, E, G, $R^1$ and $R^2$ have the meaning indicated above,
are first converted by catalytic hydrogenation on palladium/C or by reduction with $SnCl_2$ in inert solvents into the compounds of the general formula (III)

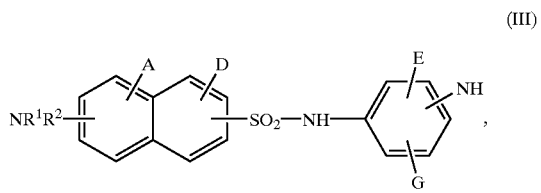

in which
A, D, E, G, $R^1$ and $R^2$ have the meaning indicated above,
and these are finally reacted with compounds of the general formula (IV)

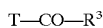 (IV)

in which
$R^3$ has the meaning indicated above
and
T represents hydroxyl or halogen,
in inert solvents, if appropriate in the presence of a base and/or of an auxiliary,
or (B) compounds of the general formula (V)

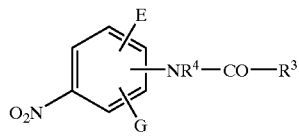

in which
E, G, $R^3$ and $R^4$ have the meaning indicated above,
are first converted as described under by hydrogenation on Pd/C or by reduction with $SnCl_2$ in inert solvents into the compounds of the general formula (VI)

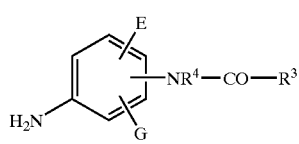

in which
E, G, $R^3$ and $R^4$ have the meaning indicated above, and these are finally reacted with compounds of the general formula (VII)

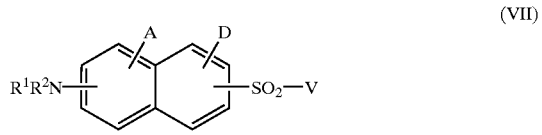

in which
A, D, $R^1$ and $R^2$ have the meaning indicated above,
and
V represents halogen,
in inert solvents, if appropriate in the presence of a base and/or of an auxiliary,
or (C) if $R^3$ and/or $R^{3'}$ represent a radical of the formula —L—O—CO—Q, compounds of the general formula (Ia)

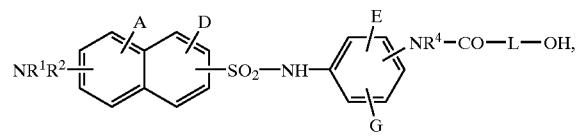

in which
$R^1$, $R^2$, $R^4$, A, D, E, G and L have the meaning indicated above
are reacted with amino acid residues of the general formula (VIII)

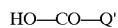 (VIII)

in which
Q' has the meaning of Q indicated above, where one of the terminal radicals on the nitrogen, mentioned there, represents one of the abovementioned protective groups,
if appropriate with activation of the carboxylic acid according to customary methods, in inert solvents and in the presence of a base and of an auxiliary,
and finally the protective group is removed according to the methods customary in peptide chemistry,
and in the case in which X, $R^4 \neq H$ is reacted with 2 or more equivalents of the compounds of the general formula (VIII),
if appropriate the stereoisomers are separated according to methods known per se and if appropriate the free bases are converted into the salts or the salts are converted into the free bases.

14. The process of claim 13 wherein T is chlorine.

15. The process of claim 13 wherein V is chlorine.

16. The process of claim 13 wherein Q' is tert-butyloxycarbonyl.

* * * * *